(12) United States Patent
Thankappan et al.

(10) Patent No.: US 9,617,280 B2
(45) Date of Patent: Apr. 11, 2017

(54) SPIRO-OXAZINES, INDOLINONES AND PREPARATION THEREOF

(71) Applicant: Council of Scientific & Industrial Research, New Delhi (IN)

(72) Inventors: Biju Akkattu Thankappan, Maharashtra (IN); Anup Bhunia, Maharashtra (IN); Tony Roy, Maharashtra (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/890,846

(22) PCT Filed: May 15, 2014

(86) PCT No.: PCT/IN2014/000327
§ 371 (c)(1),
(2) Date: Nov. 12, 2015

(87) PCT Pub. No.: WO2014/184808
PCT Pub. Date: Nov. 20, 2014

(65) Prior Publication Data
US 2016/0115179 A1    Apr. 28, 2016

(30) Foreign Application Priority Data
May 15, 2013    (IN) .......................... 1440/DEL/2013

(51) Int. Cl.
*C07D 498/20*    (2006.01)
*C07D 498/22*    (2006.01)
*C07D 401/04*    (2006.01)
*C07D 498/10*    (2006.01)

(52) U.S. Cl.
CPC ......... *C07D 498/22* (2013.01); *C07D 401/04* (2013.01); *C07D 498/10* (2013.01); *C07D 498/20* (2013.01)

(58) Field of Classification Search
CPC ... C07D 498/22; C07D 498/20; C07D 401/04
See application file for complete search history.

(56) References Cited

PUBLICATIONS

Angew. Chem. Int. Ed. 2013, 52, 10040 —10043.*

* cited by examiner

*Primary Examiner* — Kahsay Habte
(74) *Attorney, Agent, or Firm* — Lerner, David, Littenburg, Krumholz & Mentlik, LLP

(57) ABSTRACT

The present invention relates to novel spiro-oxazine analogues of Formula-I and Indolinone compounds of Formula-II or positional isomers, or stereoisomers, or derivatives, or pharmaceutically acceptable salt thereof. Formula-I Formula-II Further the invention provides transition-metal free multicomponent reaction (MCR) process for the preparation of said compounds of Formula-I and II using aryne precursor, N-substituted isatin and N-heteroaromatic compound as the nucleophile, under mild condition leading to formation of desired complex of spiro-oxazine analogues (I) and indolinone analogues (II) in high yield and selectivity.

Formula-I

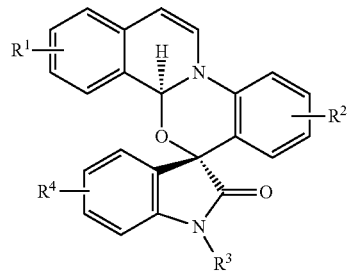

Formula-II

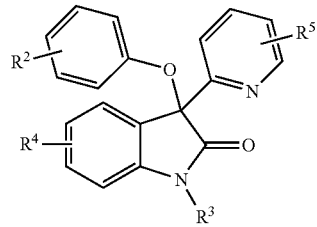

7 Claims, No Drawings

SPIRO-OXAZINES, INDOLINONES AND PREPARATION THEREOF

FIELD OF THE INVENTION

The present invention relates to novel spiro-oxazine analogues of Formula-I and Indolinone compounds of Formula-II or positional isomers, or stereoisomers, or derivatives, or pharmaceutically acceptable salt thereof.

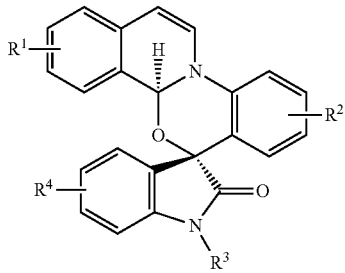

Formula-I

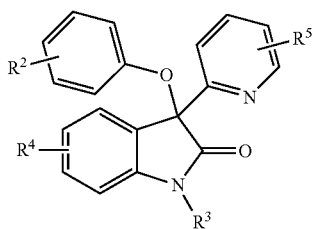

Formula-II

Further the invention provides transition-metal free multicomponent reaction (MCR) process for the preparation of said compounds of Formula-I and II using aryne precursor, N-substituted isatin and N-heteroaromatic compound as the nucleophile, under mild condition leading to formation of desired complex of spiro-oxazine analogues (I) and indolinone analogues (II) in high yield and selectivity.

BACKGROUND AND PRIOR ART OF THE INVENTION

Arynes are highly electrophilic reactive intermediates, which have been extensively utilized in various carbon-carbon and carbon-heteroatom bond-forming reactions. Arynes have been employed for the construction of multi-substituted arenes of structural diversity and complexity. This kinetically unstable intermediate can react with a wide variety of anionic and uncharged nucleophiles leading to a direct approach to access 1,2-disubstituted arenes, which are structural fragments in many natural compounds as well as biologically active compounds.

Hence the process for the preparation of these compounds and newer forms is an area of continuous research. One of the important aspects of aryne chemistry is multicomponent reaction, which mainly include the initial addition of nucleophiles to arynes and subsequent trapping of the aryl anion intermediate with electrophiles. If the nucleophile and electrophile do not belong to the same molecule, the overall process is a unique three-component coupling, where the aryne is inserted between the other two coupling partners [eqn (1)]. This versatile transition-metal-free methodology has been applied to the synthesis of valuable heterocycles and in natural product synthesis.

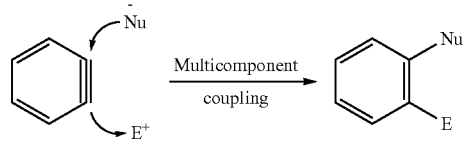

(1)

The synthesis of spirooxazine compounds using transition metal and heterocyclic compound as nucleophile is reported in the art.

KR970005311 discloses process for preparing spirooxazine compounds, comprising reacting indoline or indolinium derivatives with nitroso arene derivative to produce spirooxazine compounds characterized in that amine complex of transition metal is used as catalyst.

One-Pot Synthesis of Photochromic 6'-Amino-Substituted Spirooxazines from 1-Nitroso-2-naphthol Zinc Chelate and Indoline Base is disclosed by Pang, Mei-Li et al. in Synthesis; 2010, 20; 3418-3422. U.S. Pat. No. 4,785,097 describes process for synthesizing a spiro-type compound comprising mixing an unsubstituted or substituted first compound selected from the group consisting of 2-methyleneindoline, 2-methylenebenzothiazoline, 2-methylenebenzoxazoline, or a halide salt thereof and a metal chelate of either an ortho-hydroxynitrosoaromatic compound or a substituted ortho-hydroxynitrosoaromatic compound, the aromatic compound selected from the group consisting of benzene, naphthalene, coumarin, quinoline, isoquinoline benzofuran, benzoxazine, isocoumarin, benzopyran, pyridine or chromone, in a solvent at temperatures sufficient to cause reaction of the first compound and the metal chelate.

US20100280241 describes Spirooxazine radical derivatives and reversible isomerization reaction, where 5-member or 6-member heterocyclic ring and an oxazine derived heterocyclic ring form a Spiro structure and an oxygen radical binds to the nitrogen of the 5-member or 6-member heterocyclic ring adjacent to the spiro-carbon.

Article titled "The Three-Component Reaction between Isatin, α-Amino Acids, and Dipolarophiles" by Stanley Rehn et al. in European Journal of Organic Chemistry Volume 2004, Issue 2, pages 413-418, January 2004 discloses preparation of 3-Spiro[pyrrolidino-oxindoles] from a three-component reaction between isatin, an α-amino acid, and a dipolarophile.

Multicomponent reaction using aryne is known in the art, but utilizing N-heteroaromatic compounds as the nucleophilic trigger is very rare. However, the inventors developed novel biologically active spiro-oxazino and indolinone compounds and economically and industrially feasible process for preparation thereof, wherein the process is transition-metal free and multicomponent reaction to afford high yield and selectivity of desired products.

OBJECTS OF THE INVENTION

The main objective of the present invention relates to novel Spiro-Oxazines, Indolinones compounds and preparation thereof.

Another object of the present invention relates to a process of the invention involving multicomponent reaction using N-heteroaromatic compounds as the nucleophilic trigger.

SUMMARY OF THE INVENTION

In accordance with the objectives of invention, are disclosed novel spiro-oxazines compounds of Formula-I and indolinones compounds of Formula-II or positional isomers or stereoisomers or derivatives or pharmaceutically acceptable salt thereof.

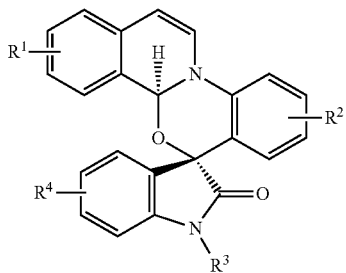

Formula-I wherein, R1 is selected from the group consisting of H, Cl, Br, F, I; R2 is selected from (C1-C6) alkyl, fluoro, or dioxane ring O—(CH2)-O; R3 represents (C1-C6) alkyl, aryl, arylalkyl, allyl; and R4 is halogen, (C1-C6) alkoxy NO2, (C2-C6) alkylene, (C1-C6) alkylaryl, aralkyl.

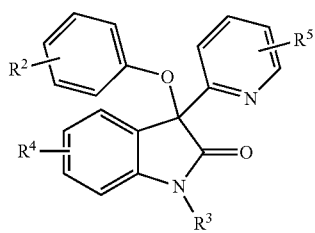

Formula-II wherein R2 is selected from (C1-C6) alkyl, fluoro, or dioxane ring O—(CH2)-O; R3 represents (C1-C6) alkyl, aryl, arylalkyl, allyl; R4 is halogen, (C1-C6) alkoxy, NO2, (C2-C6) alkylene, (C1-C6) alkyl, aryl, aralkyl and R5 is H, $N(CH_3)_2$.

In one aspect the invention provides transition-metal-free, multicomponent reaction (MCR) process for the preparation of the spiro-oxazine analogue compounds of Formula-I and indolinone analogue compounds of Formula-II comprising N-heteroaromatic compound (as the nucleophile) triggered coupling of aryne and N-substituted isatin, under mild condition to afford desired diastereoselective spiro-oxazine analogue compounds of Formula-I and indolinone analogue compounds of Formula-II.

In another aspect, the invention provides transition-metal-free, multicomponent reaction (MCR) process for the preparation of diastereoselective spiro-oxazine isoquinoline analogues of Formula-I comprising isoquinoline triggered coupling of aryne precursor and N-substituted isatin at suitable temperature in presence of fluoride source and phase transfer catalyst in suitable organic solvent.

In another aspect, the invention provides transition-metal-free, multicomponent reaction (MCR) process for the preparation of indolin-2-one analogues of Formula-II in good yield comprising pyridine initiated, coupling of aryne precursor and N-substituted isatin at suitable temperature in presence of fluoride source and phase transfer catalyst in suitable organic solvent.

DETAILED DESCRIPTION OF THE INVENTION

The invention will now be described in detail in connection with certain preferred and optional embodiments, so that various aspects thereof may be more fully understood and appreciated. In a preferred embodiment, the invention provides transition metal free multicomponent reaction (MCR) process for the preparation of spiro-oxazine compounds of Formula-I and indolinone analogue compounds of Formula-II comprising nucleophile triggered coupling of aryne precursors and N-substituted isatin, at suitable temperature under mild condition in presence of fluoride source and phase transfer catalyst in organic solvent to afford diastereoselective spiro-oxazine analogues (formula-I) and indolinone compounds (formula-II) (scheme 1).

Scheme 1:

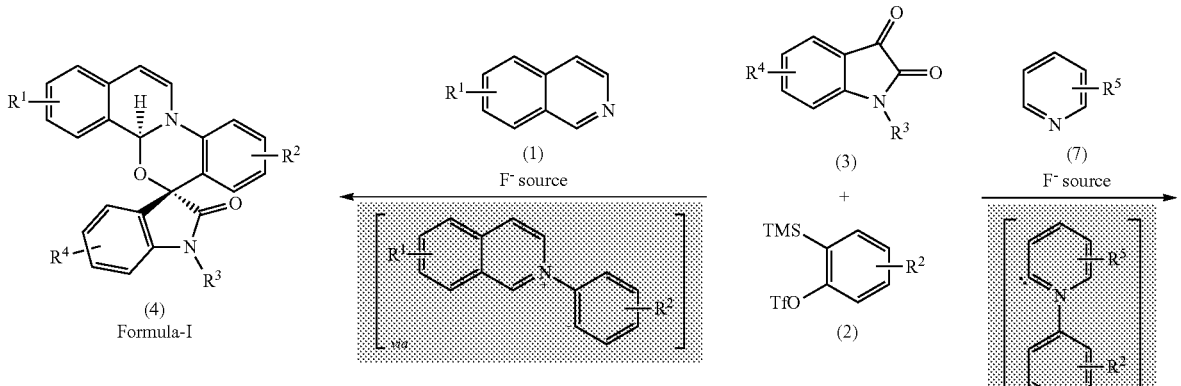

(8)
Formula-II

According to the invention, the nucleophile is preferably heterocyclic or heteroaromatic compound selected from the group consisting of substituted or unsubstituted pyridine, quinolone, isoquinoline, the substituents are selected from halogen, or secondary amine.

Further the N-substituted isatin used in the instant MCR having formula (3).

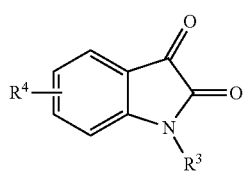

3 where R3 represents (C1-C6) alkyl, aryl, arylalkyl, allyl; R4 is halogen, (C1-C6) alkoxy, NO2, (C2-C6) alkylene, (C1-C6) alkyl, aryl, aralkyl.

The instant transitional metal free, multicomponent reaction process, wherein the aryne precursor is substituted or unsubstituted 2-(trimethylsilyl)aryl triflate of Formula (2).

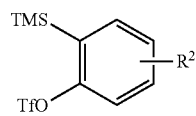

2 where R2 is selected from (C1-C6) alkyl, halogen, or dioxane ring O—(CH2)-O. According to the process the fluoride source is preferably KF and phase transfer catalyst is 1,4,7,10,13,16-hexaoxacyclooctadecane, wherein the aryne substrate is generated in situ from aryne precursor i.e. 2-(trimethylsilyl)aryl triflate 2 by using KF and 1,4,7,10,13,16-hexaoxacyclooctadecane. The suitable organic solvent is THF, Ethyl acetate, DMF, DCM, Acetone. The temperature maintained during the course of reaction is in between 20° to 100° C., preferably 25° to 75° C. In accordance to the process, the multicomponent reactions involving aryne precursors (2), isatins (3) with isoquinoline (1) as the nucleophilic trigger, the reaction afforded the spirooxazino isoquinoline derivatives (4) proceeding via 1,4-dipolar intermediates. On the other hand the utility of pyridine moiety (7) as nucleophile furnished indolin 2-one derivatives (8) and the reaction is likely to proceed through a pyridylidene intermediate. The instant MCR is occurred which leads to the formation of the spirooxazino isoquinoline derivatives (4) as an inseparable mixture of diastereomers, wherein the major and desired diastereomer is separated by known process like crystallization and its structure and stereochemistry is unequivocally confirmed by single-crystal X-ray analysis.

According to the above embodiment, the novel biologically active compounds of formula-I encompasses the compounds (4a-4p) listed herein below table 1.

TABLE 1

| Compounds | Structure | Diastereomeric ratio | Yield |
|---|---|---|---|
| 4a | 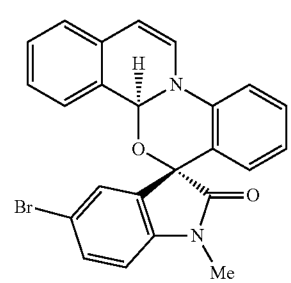 | (9:1) | 63% |

TABLE 1-continued

| Compounds | Structure | Diastereomeric ratio | Yield |
|---|---|---|---|
| 4b | 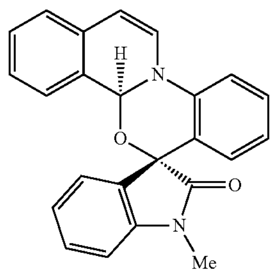 | (4:1) | 71% |
| 4c | 4c | (6:1) | 77% |
| 4d | 4d | (6:1) | 60% |
| 4e | 4e | (4:1) | 69% |

TABLE 1-continued

| Compounds | Structure | Diastereomeric ratio | Yield |
|---|---|---|---|
| 4f | 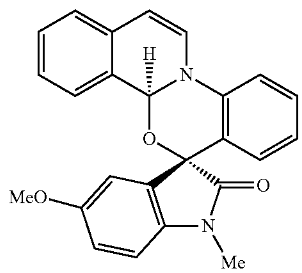 | (5:1) | 72% |
| 4g | 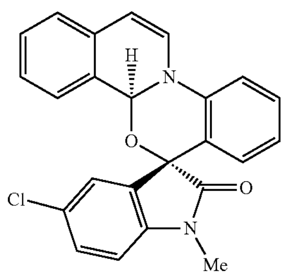 | (5:1) | 81% |
| 4h | 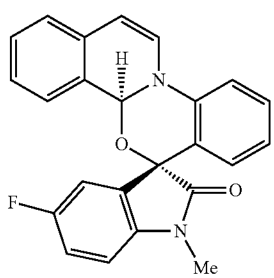 | (6:1) | 69% |
| 4i | 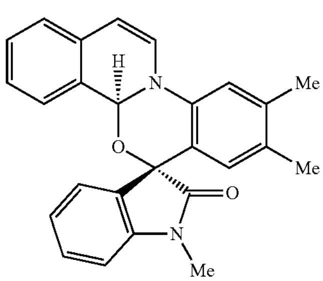 | (6:1)$^a$ | 74% |
| 4j | 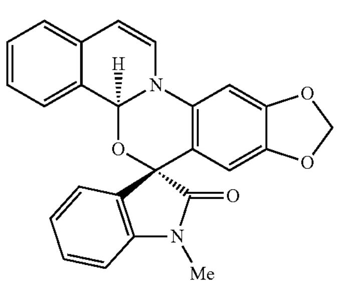 | (10:1)$^a$ | 67% |

TABLE 1-continued

| Compounds | Structure | Diastereomeric ratio | Yield |
|---|---|---|---|
| 4k | 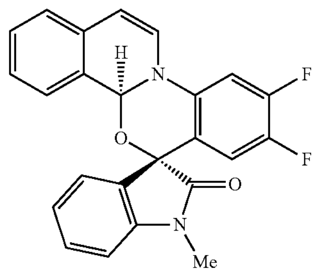 | (12:1)[a] | 70% |
| 4l | 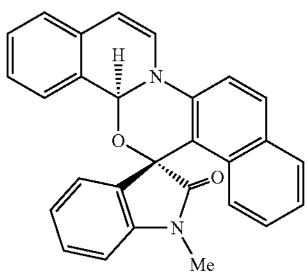 | (5:1) | 76% |
| 4m | 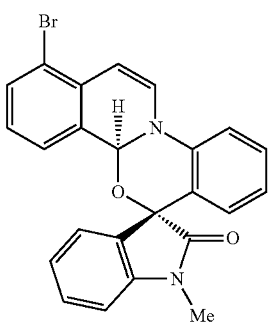 | (>20:1) | 90% |
| 4n | 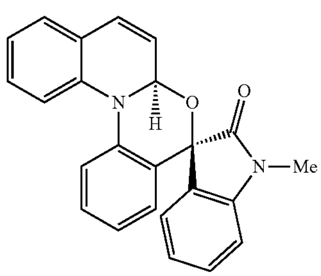 | (>20:1) | 49% |
| 4o | 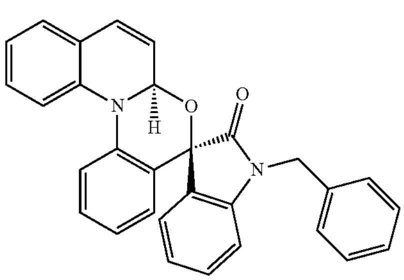 | (>20:1)[b] | 63% |

[a]Reaction was run on 0.25 mmol scale.
[b]Reaction run using 2.0 equiv of quinoline and 2.0 equiv of 2a.

According to the invention, the novel spiro-oxazino analogues of Formula-I compounds (4) are selected from the group consisting of;
i. 5'-bromo-1'-methyl-4bH-spiro[benzo[4,5][1,3]oxazino[2,3-a]isoquinoline-6,3'-indolin]-2'-one (4a);
ii. 1'-Methyl-4bH-spiro[benzo[4,5][1,3]oxazino[2,3-a]isoquinoline-6,3'-indolin]-2'-one (4b);
iii. 1'-Benzyl-4bH-spiro[benzo[4,5][1,3]oxazino[2,3-a]isoquinoline-6,3'-indolin]-2'-one (4c);
iv. 1'-Allyl-4bH-spiro[benzo[4,5][1,3]oxazino[2,3-a]isoquinoline-6,3'-indolin]-2'-one (4d);
v. 1'-Phenyl-4bH-spiro[benzo[4,5][1,3]oxazino[2,3-a]isoquinoline-6,3'-indolin]-2'-one (4e);
vi. 5'-Methoxy-1'-methyl-4bH-spiro[benzo[4,5][1,3]oxazino[2,3-a]isoquinoline-6,3' indolin]-2'-one (4f);
vii. 5'-Chloro-1'-methyl-4bH-spiro[benzo[4,5][1,3]oxazino[2,3-a]isoquinoline-6,3'-indolin]-2'-one (4g);
viii. 5'-fluoro-1'-methyl-4bH-spiro[benzo[4,5][1,3]oxazino[2,3-a]isoquinoline-6,3'-indolin]-2'-one (4h);
ix. 1',8,9-Trimethyl-4bH-spiro[benzo[4,5][1,3]oxazino[2,3-a]isoquinoline-6,3'-indolin]-2'-one (4i);
x. 1-Methyl-4b'H-spiro[indoline-3,6'-[1,3]dioxolo[4",5":4',5']benzo[1',2':4,5][1,3]oxazino[2,3-a]isoquinolin]-2-one (4j);
xi. 8,9-Difluoro-1'-methyl-4bH-spiro[benzo[4,5][1,3]oxazino[2,3-a]isoquinoline-6,3' indolin]-2'-one (4k);
xii. 1-Methyl-13b'H-spiro[indoline-3,15'-naphtho[2',1':4,5][1,3]oxazino[2,3-a]isoquinolin]-2-one (4l);
xiii. 1-Bromo-1'-methyl-4bH-spiro[benzo[4,5][1,3]oxazino[2,3-a]isoquinoline-6,3'-indolin]-2'-one (4m);
xiv. 1'-Methyl-6aH-spiro[benzo[4,5][1,3]oxazino[3,2-a]quinoline-5,3'-indolin]-2'-one (4n);
xv. 1'-Benzyl-6aH-spiro[benzo[4,5][1,3]oxazino[3,2-a]quinoline-5,3'-indolin]-2'-one (4o);

In yet another preferred embodiment, the invention provides transition-metal free multicomponent reaction, process for preparation of spirooxazino isoquinoline compounds of Formula-I (compounds 4a-4o).

Accordingly, the process comprises isoquinoline (1) triggered coupling of aryne precursor (2) and N-substituted isatine compounds (3), in presence of KF and in THF as solvent at 70° C. The time required to accomplish the reaction is about 24 hrs. More particularly 1.0 equivalent of compound (1) is used to initiate the coupling reaction of 1.5 equivalents of aryne precursor (2) and 1.0 equivalent of compound (3), accompanied by 3.0 equiv. of 1,4,7,10,13,16-hexaoxacyclooctadecane and KF each to obtain diastereomeric mixture of spiro-oxazino compounds (4) where the desired diastereomer is isolated by crystallization. Further when quinoline is used to trigger the multi-component reaction, the molar concentration is increased to 2 equivalents with 2 equivalents of aryne precursor (Scheme-2).

Scheme-2:

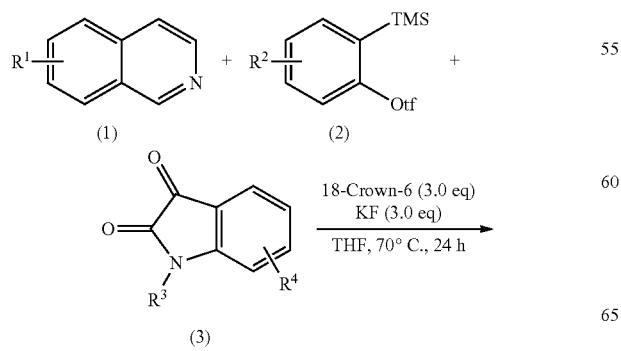

(4)

Formula-I

MCR involving isoquinoline, arynes and N-substituted isatins: reaction scope. General conditions: 1 (0.5 mmol), 2 (0.75 mmol), 3 (0.5 mmol) KF (1.5 mmol), [18]crown-6 (1.5 mmol), THF (2.0 mL), 70° C., 24 h. Total yields of both diastereomers are given and shown is major diastereomer. Diastereomeric ratio determined by ¹H NMR analysis of crude reaction mixture.

In typical embodiment, the invention provides transition metal free, MCR process for preparation of 4a, wherein 1 eqv. of 5-bromo-1-methylindoline-2,3-dione 3a coupled with 1.5 eqv. of 2-(trimethylsilyl)aryl triflate 2a activated by 1.0 eqv. of isoquinoline in presence of 3.0 eqv. of 1,4,7,10,13,16-hexaoxacyclooctadecane and KF each and THF at 70° C. for 24 hrs to obtain 63% diastereomeric mixture of 4a in 9:1 ratio, wherein the major diastereomer is desired. The major diastereomer 4a is separated by crystallization and its structure and stereochemistry is unequivocally confirmed by single-crystal X-ray analysis (cf scheme 3).

Scheme 3:

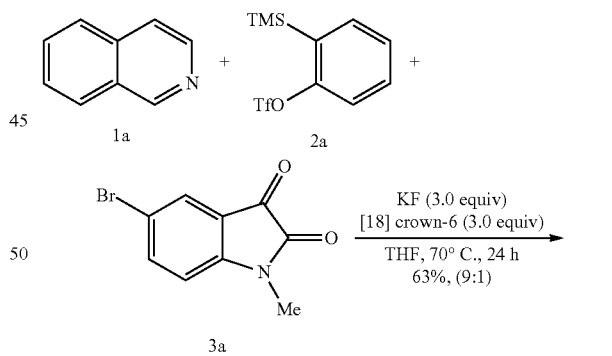

With regards to the instant three-component coupling reaction, substrate scope of isoquinoline triggered aryne MCR is evaluated.

It is found that, the reaction is well tolerated by various substituents on the isatin nitrogen leading to inseparable mixture of spirooxazino isoquinoline derivatives in 60-77% yield and moderate diastereoselectivity (4b-4e). Moreover, electron releasing and -withdrawing groups at the carbocyclic ring of isatin resulted in the better conversion to the product (4f-4h). Additionally, electronically different 4,5-disubstituted symmetrical arynes readily afforded the spirooxazino isoquinoline derivatives in good yields and diastereoselectivities (4i-4k). Further, an unsymmetric aryne generated from 1-(trimethylsilyl)-2-naphthyltriflate furnished the desired product in 76% yield in a 5:1 ratio (4l). In this case, the observed regioselectivity may be due to the addition of isoquinoline to the least hindered position of naphthalyne. Furthermore, instant unique MCR is not limited to isoquinoline, but also 5-bromoisoquinoline as well as quinoline worked well leading to the formation of the desired products in moderate to good yields (4m, 4n, 4o).

Alternatively, the isatin component of the reaction can be replaced with trifluoro acetophenone leading to good yield of the trifluoromethylated product (4p), thereby significantly expanding the scope of instant MCR.

It is noteworthy that, the said MCR is carried out via the initial generation of the 1,4-dipolar intermediate 5 from isoquinoline and aryne (generated from 2). The zwitterion 5 can add to the electrophilic carbonyl group of isatin in a concerted manner leading to the formation of 4. Alternatively, in a step-wise pathway, 5 can add to isatin generating the tetrahedral intermediate 6, which undergoes cyclization leading to formation of 4. The observed diastereoselectivity in the process sheds light on a step-wise pathway (Scheme 4).

According to the above embodiment, the novel biologically active indolinone compounds of formula-II (8) encompass the compounds listed herein below table 2.

TABLE 2

| Compound | Structure | Yield |
| --- | --- | --- |
| 8a | 8a | 79% |
| 8b | 8b | 74% |

Scheme 4:

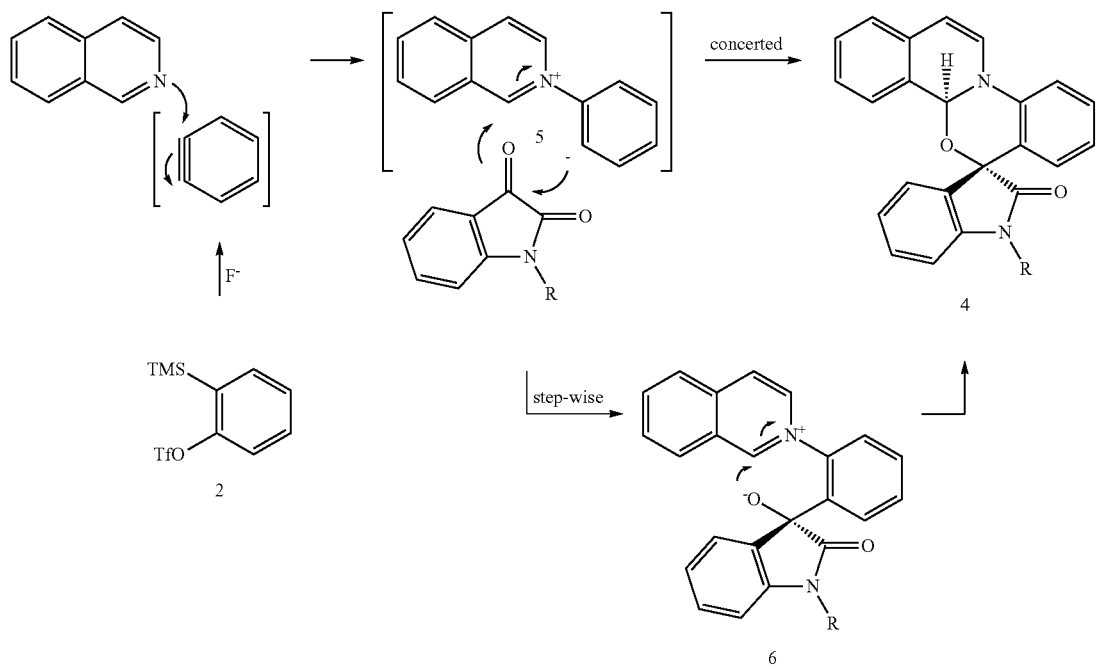

TABLE 2-continued

| Compound | Structure | Yield |
|---|---|---|
| 8c | 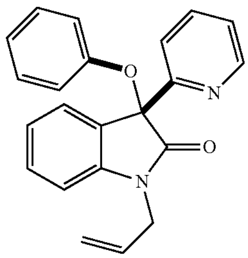 | 73% |
| 8d | 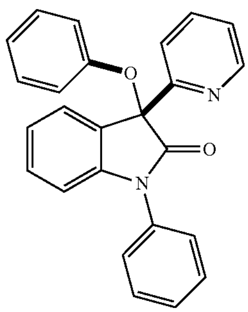 | 69%[a] |
| 8e | 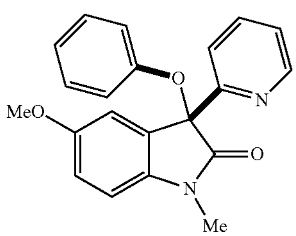 | 77% |
| 8f | 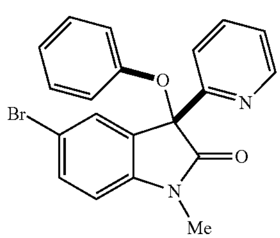 | 74% |
| 8g | 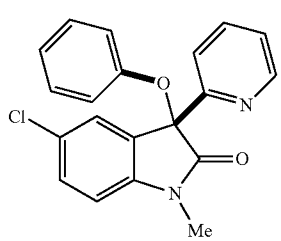 | 68% |
| 8h | 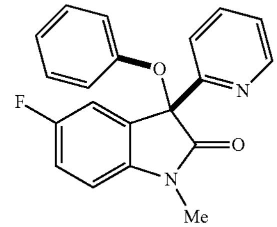 | 68% |
| 8i | 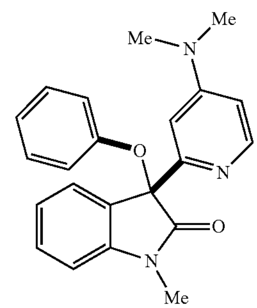 | 89% |
| 8j | 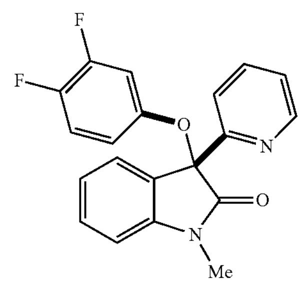 | 71%[b] |

[a] 1H-NMR yield of the product is given.
[b] Reaction was run on 0.25 mmol scale.

According to the invention, the novel indolinone compounds of Formula-I (8a-8j) are selected from the group consisting of;
i. 1-Methyl-3-phenoxy-3-(pyridin-2-yl)indolin-2-one (8a);
ii. 1-Benzyl-3-phenoxy-3-(pyridin-2-yl)indolin-2-one (8b);
iii. 1-Allyl-3-phenoxy-3-(pyridin-2-yl)indolin-2-one (8c);
iv. 3-Phenoxy-1-phenyl-3-(pyridin-2-yl)indolin-2-one (8d);
v. 5-methoxy-1-methyl-3-phenoxy-3-(pyridin-2-yl)indolin-2-one (8e);
vi. 5-Bromo-1-methyl-3-phenoxy-3-(pyridin-2-yl)indolin-2-one (8f);
vii. 5-Chloro-1-methyl-3-phenoxy-3-(pyridin-2-yl)indolin-2-one (8g);
viii. 5-Fluoro-1-methyl-3-phenoxy-3-(pyridin-2-yl)indolin-2-one (8h);
ix. 3-(4-(Dimethylamino)pyridin-2-yl)-1-methyl-3-phenoxyindolin-2-one (8i);
x. 3-(3,4-Difluorophenoxy)-1-methyl-3-(pyridin-2-yl)indolin-2-one (8j).

In yet another preferred embodiment, the invention provides transition-metal free multicomponent reaction, process for preparation of indolinone/pyridooxazino Compounds of Formula-II (8a-8j).

The indolinone analogues of Formula II can also be referred as pyridooxazino analogues.

Scheme 5:

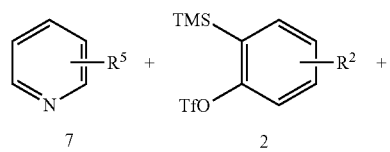

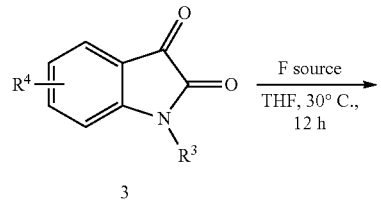

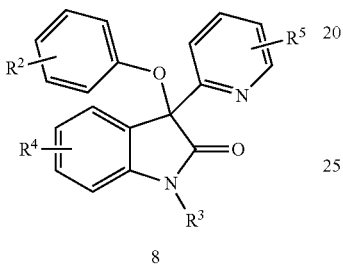

Scheme: 6

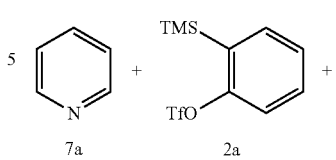

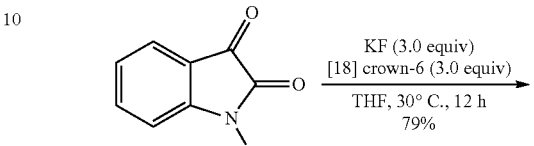

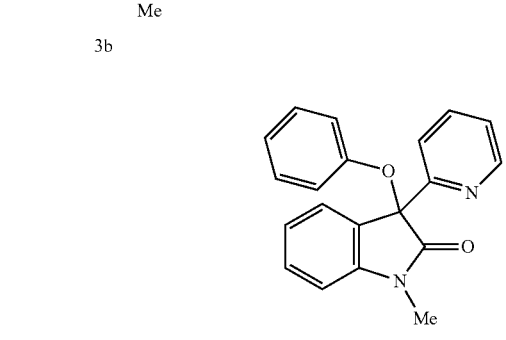

MCR involving pyridine, arynes and N-substituted isatins: reaction scope. General conditions: 7 (0.75 mmol), 2 (0.75 mmol), 3 (0.5 mmol) KF (1.5 mmol), 1,4,7,10,13,16-hexaoxacyclooctadecane (1.5 mmol), THF (2.0 mL), 30° C., 12 h.

Accordingly, the process comprises pyridine (7) as nucleophile to trigger the coupling of aryne precursor (2) and N-substituted isatine compounds (3), in presence of KF and 1,4,7,10,13,16-hexaoxacyclooctadecane in THF as solvent, under ambient temperature of about 30° C. The time required to accomplish the reaction is about 12 hrs.

More particularly, 1.5 equivalent of pyridine compound (7) is used to initiate the coupling reaction 1.5 equivalents of aryne precursor (2) and 1.0 equivalent of isatin compound (3), accompanied by 3.0 eqv. of 1,4,7,10,13,16-hexaoxacyclooctadecane and KF each and 1-5 ml of THF to obtain desired indolinone analogues of Formula-II i.e. compounds (8a-8j).

In typical embodiment, the invention provides MCR process for preparation of 8a, wherein 1.0 eqv. of 1-methylindoline-2,3-dione 3b coupled with 1.5 eqv. of 2-(trimethylsilyl)aryl triflate 2a which is activated by 1.5 eqv. of pyridine 7a in presence of 3.0 eqv. of 1,4,7,10,13,16-hexaoxacyclooctadecane and KF each and THF at 30° C. for 12 hrs to obtain 79% yield of 1-Methyl-3-phenoxy-3-(pyridin-2-yl)indolin-2-one (8a). The said reaction proceeds via a conceptually new heteroarylation followed by arylation reaction of isatin involving the C—H bond functionalization of pyridine and an intramolecular aryl transfer reaction. It is noteworthy that no product derived from the initial generation of 1,4-dipolar intermediate from pyridine and aryne (analogous to 5) and its interception with isatin is observed. Further the structure of 8a is confirmed by single-crystal X-ray analysis (cf Scheme 6).

To extend the scope of the instant process, various substituents on isatin nitrogen are employed to MCR initiated by pyridine that resulted in the easy conversion to the indolin 2-one derivatives (8b-8d). In addition, electron releasing and -withdrawing groups at the carbocyclic ring of isatin are well tolerated leading to the desired products in moderate to good yields (8e-8h). Further 4-dimethylamino pyridine (DMAP) can be used as the nucleophile affording the indolin-2-one. (8i) in 89% yield. Furthermore, 4,5-difluorobenzyne also furnished the desired product (8j) in 71% yield demonstrating the versatility of the present reaction.

In an additional embodiment, the pyridine 7a initiated reaction was carried out using 4,5-disubstituted symmetrical aryne precursor 2c, which did not afford the expected indolin 2-one derivative (8l), but instead furnished the N-aryl pyridin-2-one derivative (9a) in moderate yield (cf Scheme 7).

Scheme 7:

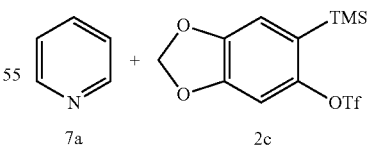

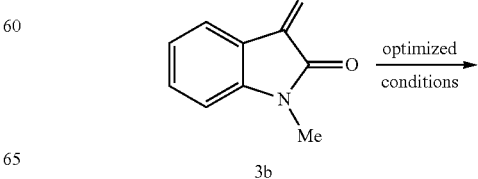

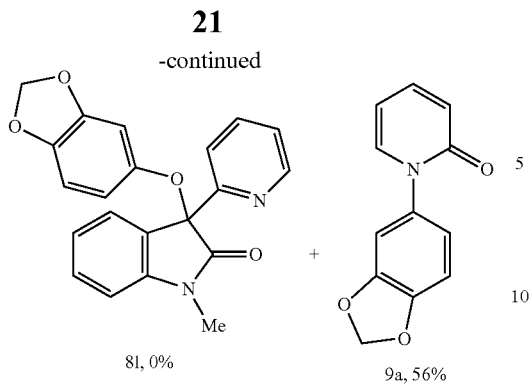

8l, 0%   9a, 56%

Since 9a was formed from pyridine and aryne without incorporating isatin, The additional experiments was carried out without adding isatin. After mixing of pyridine and the aryne precursor 2b under the optimized conditions to afford 9a in 79% yield Scheme 8. Similar results were obtained with aryne precursor 2c. These results tend to indicate that the initially generated 1,4-dipolar intermediate between pyridine and aryne (instead of adding to isatin) undergo an intramolecular proton transfer to form highly nucleophilic pyridylidene intermediate 10, which was likely quenched by atmospheric oxygen to form the pyridine-2-one derivatives (cf Scheme 8):

Scheme 8:

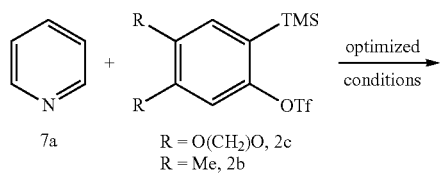

7a    R = O(CH$_2$)O, 2c
      R = Me, 2b

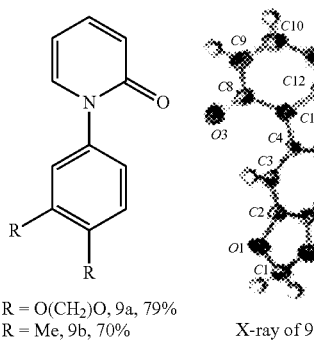

R = O(CH$_2$)O, 9a, 79%
R = Me, 9b, 70%    X-ray of 9a    10

Moreover, to get further mechanistic insight on the participation of pyridylidene 10 in reaction, an experiment was carried out using pyridine-d5 11, 12 in 65% yield with incorporation of deuterium at 2-position of the aryl group as depicted in Scheme 9:

Scheme 9:

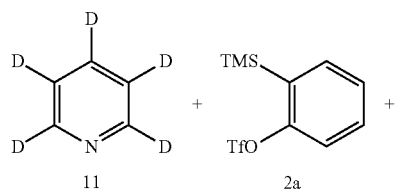

11    2a

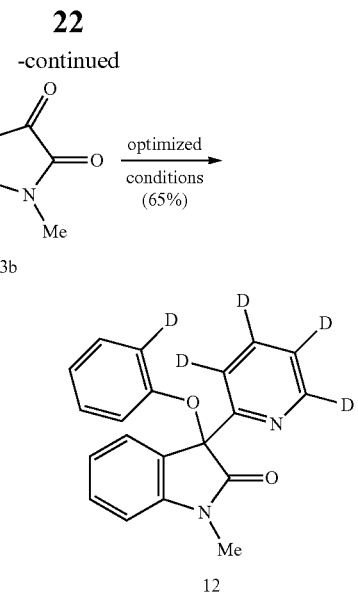

3b

12

Further, the mechanism of said MCR involves first, nucleophilic attack of pyridine on aryne generates the 1,4-dipolar intermediate 13. In the absence of external proton source, 13 undergo an intramolecular proton transfer to generate the pyridylidene intermediate 10. The nucleophilic intermediate 10 adds to isatin generating the tetrahedral intermediate 14, which on intramolecular nucleophilic aromatic substitution ($S_NAr$) reaction to furnish the indolin 2-one 8 via the σ-complex 15 (cf scheme 10).

Scheme 10:

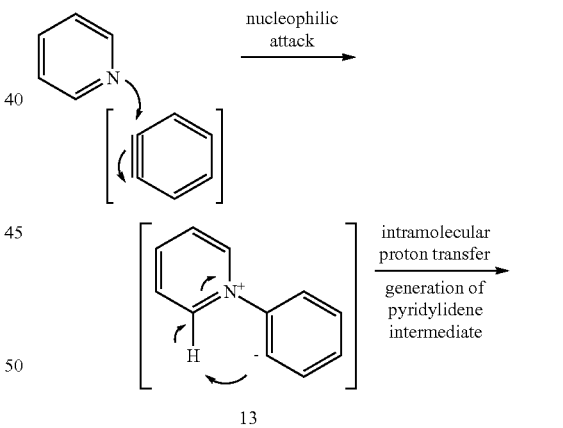

13

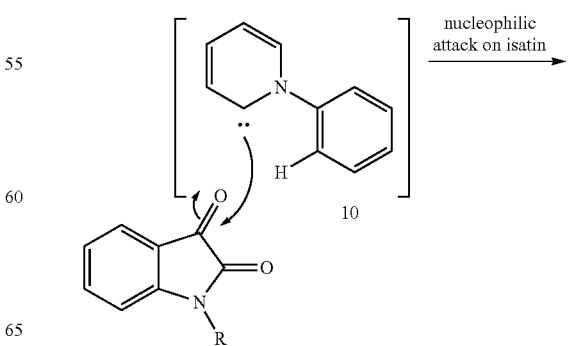

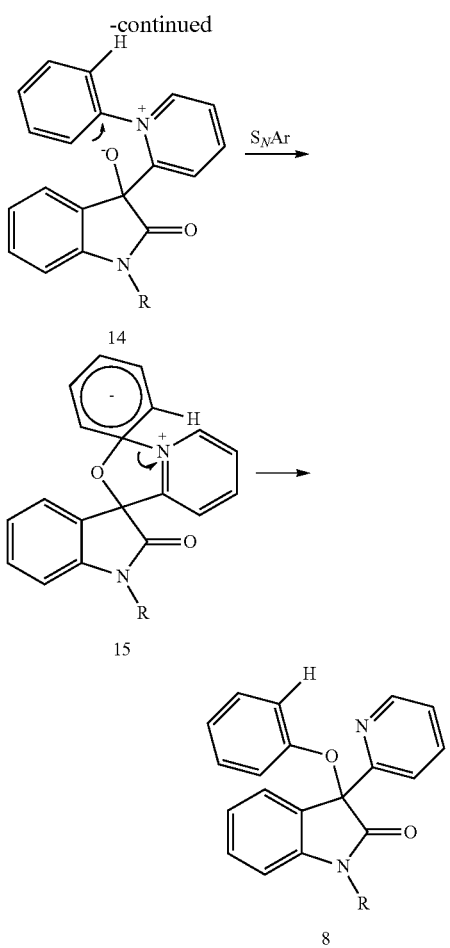

According to the invention the process uses multicomponent reaction using N-heteroaromatic compound as the nucleophile leading to the formation of complex spiro-oxazine and indolinone moiety.

The process of the invention is characteristic in generating mild aryne leading to spiro-oxazine and indolinone under transition-metal-free conditions. Consequently, the inventors have developed a conceptually new MCR involving arynes, N-heterocycles and N-substituted isatins. When isoquinoline is used as the nucleophile, the reaction furnished the spirooxazino isoquinoline derivatives and the reaction proceeds via 1,4-dipolar intermediates and when pyridine is used as nucleophilic trigger, the reaction afforded indolin 2-one derivatives and the reaction is likely to proceed through a pyridylidene intermediate.

The novel spiro-oxazine of Formula-I and indolinone compounds of Formula-II disclosed may be core of several biologically active compounds. Spiro oxazines as a class of compounds are known for kinase inhibition activity and compounds of the invention may find use in similar applications.

EXPERIMENTAL

Unless otherwise specified, all reactions were carried out under an atmosphere of argon in flame-dried reaction vessels with Teflon screw caps. Reaction temperatures are reported as the temperature of the bath surrounding the reaction vessel. 30° C. corresponds to the room temperature of the lab when the experiments were carried out. THF was freshly purified by distillation over Na-benzophenone and was transferred under argon. 1,4,7,10,13,16-hexaoxacyclooctadecane was recrystallized from dry CH3CN and KF was dried by heating at 110° C. for 12 h and left to cool under argon. The isatin derivatives were purchased from Sigma Aldrich or Acros and the N-alkylation was carried out by treating with the corresponding alkyl halides under basic condition following the known procedure.

Isoquinoline and quinoline were purchased from Aldrich and was purified by distillation prior to use. Dry pyridine was purchased from local sources and was purified by distillation and was stored under KOH. The 2(trimethylsilyl)phenyl trifluoromethane sulfonate 2a and the other symmetric and unsymmetric aryne precursors were synthesized following literature procedure.

Analytical thin layer chromatography was performed on TLC Silica gel 60 F254. Visualization was accomplished with short wave UV light or KMnO4 staining solutions followed by heating. Chromatography was performed on silica gel (230-400 mesh) by standard techniques eluting with solvents as indicated.

All compounds were fully characterized. 1H and 13C NMR spectra were recorded on Bruker AV 400, 500 in solvents as indicated. Chemical shifts (δ) are given in ppm. The residual solvent signals were used as references and the chemical shifts converted to the TMS scale (CDCl3: δH=7.26 ppm, δC=77.16 ppm). Infrared spectra were recorded on a Perkin-Elmer 1615 FT Infrared Spectrophotometer Model 60B. The wave numbers (n) of recorded IR-signals are quoted in cm-1. HRMS data were recorded on a Thermo Scientific Q-Exactive, Accela 1250 pump.

EXAMPLES

The invention will now be illustrated with help of examples. The aforementioned embodiments and below mentioned examples are for illustrative purpose and are not meant to limit the scope of the invention.

Example 1

To a flame-dried screw-capped test tube equipped with a magnetic stir bar was added 1,4,7,10,13,16-hexaoxacyclooctadecane (0.396 g, 1.5 mmol), KF (0.087 g, 1.5 mmol) and 1-methylindoline-2,3-dione 3 (0.50 mmol). Then the screw-capped tube was evacuated and backfilled with argon. The mixture was dissolved in THF (2.0 mL) under argon atmosphere. The resultant reaction mixture was kept stirring at 30° C. for 5 min. To the stirring solution was then added isoquinoline 1 (0.50 mmol) and the aryne precursor 2 (0.75 mmol). Then the reaction mixture was placed in preheated oil bath at 70° C. When TLC control showed the completion of the reaction (typically after 24 h), the reaction mixture cooled to room temperature and the solvent was evaporated and the crude residue was subsequently purified by flash column chromatography on silica gel to afford the corresponding spirooxazino isoquinoline derivatives (4) as an inseparable mixture of diastereomers in moderate to good yields. The dr was determined by 1H NMR analysis of crude reaction mixture.

Example 2

General Procedure for the MCR Involving Pyridine, Aryne and Isatin

To a flame-dried screw-capped test tube equipped with a magnetic stir bar was added 1,4,7,10,13,16-hexaoxacyclooctadecane (0.396 g, 1.5 mmol), KF (0.087 g, 1.5 mmol) and 1-methylindoline-2,3-dione 3 (0.50 mmol). Then the screw-capped tube was evacuated and backfilled with argon. The mixture was dissolved in THF (2.0 mL) under argon atmosphere. The resultant reaction mixture was kept stirring at 30° C. for 5 min. To the stirring solution was added pyridine 7 (0.75 mmol) and the aryne precursor 2 (0.75 mmol). When TLC control showed the completion of the reaction (typically after 12 h), the reaction stopped and the crude reaction mixture was purified by column chromatography on silica gel to afford the corresponding indolin 2-one derivatives 8 in good yields.

Example 3

Attempted Multicomponent Reaction of Pyridine with Electronically Different Aryne Precursor and Isatin To a flame-dried screw-capped test tube equipped with a magnetic stir bar was added 11,4,7,10,13,16-hexaoxacyclooctadecane (0.396 g, 1.5 mmol), KF (0.087 g, 1.5 mmol) and 1-methylindoline-2,3-dione 3 (0.50 mmol). Then the screw-capped tube was evacuated and backfilled with argon. The mixture was dissolved in THF (2.0 mL) under argon atmosphere. The resultant reaction mixture was kept stirring at 30° C. for 05 min. To the stirring solution was added pyridine 7a (0.75 mmol) and 6-(trimethylsilyl)benzo[d][1,3]dioxol-5-yl trifluoromethanesulfonate 2c (0.75 mmol) and the reaction mixture was stirred for 12 h. The crude reaction mixture was then purified by column chromatography on silica gel to afford the 1-(benzo[d][1,3]dioxol-4-yl)pyridin-2(1H)-one 9a in 56% yield. Interestingly, under the reaction conditions, the multicomponent product 8l was not observed.

This result tends to indicate that as the electron richness of the benzene ring in 2c increases, there is less probability of the intramolecular nucleophilic aromatic substitution (SNAr) [Scheme 6 of manuscript, the formation of σ-complex 15 from 14]. In addition, the generated pyridylidene intermediate was quenched by atmospheric oxygen to furnish 9a.

Example 4

Attempted Multicomponent Reaction of Pyridine with Aryne Precursor (2b) and Isatin Under Degassing Condition To a flame-dried screw-capped test tube equipped with a magnetic stir bar was added 11,4,7,10,13,16-hexaoxacyclooctadecane (0.396 g, 1.5 mmol) KF (0.087 g, 1.5 mmol) and 1-methylindoline-2,3-dione 3b (0.080 g, 0.50 mmol). Then the screw-capped tube was evacuated and backfilled with argon. The mixture was dissolved in THF (2.0 mL) under argon atmosphere followed by the addition of pyridine 7a (0.060 mg, 60 μL, 0.75 mmol). Then the resultant reaction mixture was subjected to degassing (freeze-pump-thaw cycles). The resultant reaction mixture was kept stirring at 30° C. for 5 min. To the stirring solution was 4,5-dimethyl-2-(trimethylsilyl)phenyl trifluoromethane sulfonate 2b (0.244 g, 0.75 mmol) and the reaction mixture was stirred at 30° C. for 12 h. The crude reaction mixture was then purified by flash column chromatography on silica gel to afford the 1-(3,4-dimethylphenyl)pyridin-2(1H)-one 9b in <10% yield and 89% of the isatin derivative 3b was recovered. Interestingly, under the reaction conditions, the multicomponent product 8l was not observed.

Example 5

Reaction of Arynes with Pyridine

To a flame-dried screw-capped test tube equipped with a magnetic stir bar was added 18-crown-6 (0.198 g, 0.75 mmol) and KF (0.043 g, 0.75 mmol). Then the screw-capped tube was evacuated and backfilled with argon. The mixture was dissolved in THF (1.0 mL) under argon atmosphere. The resultant reaction mixture was kept stirring at 30° C. for 05 min. To the stirring solution was added pyridine 7a (0.75 mmol) and aryne precursors 2c or 2b (0.75 mmol) and stirred the reaction mixture for 12 h. The reaction stopped after 12 h and the crude reaction mixture was purified by column chromatography on silica gel to afford pyridin-2(1H)-one 9a and 9b.

This experiment tends to indicate the generation of the pyridylidene intermediate from aryne and pyridine, which was subsequently quenched by atmospheric oxygen to furnish 9a and 9b.

Example 6

Attempted Reaction of Pyridine with Aryne Precursor in the Presence of Sulphur flame-dried screw-capped test tube equipped with a magnetic stir bar was added 11,4,7,10,13,16-hexaoxacyclooctadecane (0.396 g, 1.5 mmol) and KF (0.087 g, 1.5 mmol). Then the screw-capped tube was evacuated and backfilled with argon. The mixture was dissolved in THF (2.0 mL) under argon atmosphere followed by the addition of pyridine 7a (0.040 mg, 54 μL, 0.50 mmol). Then the resultant reaction mixture was subjected for degassing (freeze-pump-thaw cycles). The resultant reaction mixture was kept stirring at 30° C. for 5 min. To the stirring solution was 2-(trimethylsilyl)phenyl trifluoromethanesulfonate 2a (0.223 g, 182 μL, 0.75 mmol) and the reaction mixture was stirred at 30° C. for 2 h followed by the addition of sulphur (0.032 g, 1.0 mmol) and stirred the reaction mixture for 12 h. The crude reaction mixture was then purified by flash column chromatography (Pet. ether/EtOAc=75/25) on silica gel to afford the 1-phenylpyridine-2(1H)-thione as a yellow solid (0.015 g, 16% yield).

Rf (Pet. ether/EtOAc=30/70): 0.32; 1H NMR (500 MHz, CDCl3) δ 7.76 (d, J=8.8 Hz, 1H), 7.61 (bs, 1H), 7.54 (t, J=7.3 Hz, 2H), 7.49 (t, J=7.3 Hz, 1H), 7.34 (d, J=7.5 Hz, 2H), 7.28-7.26 (m, 1H), 6.70 (bs, 1H). 13C NMR (125 MHz, CDCl3) δ 181.38, 143.83, 139.75, 135.71, 133.39, 128.74, 128.28, 125.59, 111.75. HRMS calculated [M+H]+ for C11H10SN: 188.0528. found: 188.0529. FTIR (cm-1) 3061, 3016, 1715, 1635, 1612, 1567, 1488, 1471, 1421, 1369, 1347, 1300, 1251, 1217, 1130, 1091, 1025, 1001, 977, 953, 752, 691, 666.

This experiment is an evidence for the formation of the pyridylidene intermediate. The pyridylidene intermediate is quenched by sulphur to furnish the thione.

Example 7

Reaction of Pyridine-d5 with Aryne and Isatin

To a flame-dried screw-capped test tube equipped with a magnetic stir bar was added 1,4,7,10,13,16-hexaoxacyclooctadecane (0.396 g, 1.5 mmol), KF (0.087 g, 1.5 mmol) and 1-methylindoline-2,3-dione 3b (0.080 g, 0.50 mmol). Then the screw-capped tube was evacuated and backfilled with argon. The mixture was dissolved in THF (2.0 mL) under argon atmosphere. The resultant reaction mixture was kept stirring at 30° C. for 5 min. To the stirring solution was added pyridine-d5 11 (0.063 g, 60 µL, 0.75 mmol) and the aryne precursor 2a (0.223 g, 182 µL, 0.75 mmol). When TLC control showed the completion of the reaction (typically after 12 h), the reaction stopped and the crude reaction mixture was purified by column chromatography on silica gel to afford the corresponding indolin 2-one derivatives 12 in 65% yield.

Example 8

Synthesis and Characterization of Spirooxazino Isoquinolines

5'-bromo-1'-methyl-4bH-spiro[benzo[4,5][1,3]oxazino[2,3-a]isoquinoline-6,3'-indolin]-2'-one (4a)

Following the general procedure, treatment of isoquinoline 1a (0.129 g, 118 µL, 1.0 mmol) and 5-bromo-1-methylindoline-2,3-dione (0.240 g, 1.0 mmol) with 2-(trimethylsilyl)phenyl trifluoromethane sulfonate 2a (0.447 g, 364 µL, 1.5 mmol) in the presence of KF (0.174 g, 3.0 mmol) and 1,4,7,10,13,16-hexaoxacyclooctadecane (0.793 g, 3.0 mmol) in THF (4.0 mL) at 70° C. for 24 h followed by flash column chromatography (Pet. ether/EtOAc=93/07) of the crude reaction mixture afforded 5'-bromo-1'-methyl-4bH-spiro[benzo[4,5][1,3]oxazino[2,3-a]isoquinoline-6,3'-indolin]-2'-one as inseparable mixture of diastereomers as a white solid (0.281 g, 63%, dr determined by 1H NMR analysis of crude reaction mixture is 9:1). CCDC-938921 (4a) contains the supplementary crystallographic data for this paper. Rf (Pet. ether/EtOAc=70/30): 0.63 1H NMR (400 MHz, CDCl3) δ 7.45-7.39 (m, 3H), 7.35-7.29 (m, 3H), 7.21-7.11 (m, 3H), 7.00-6.96 (m, 1H), 6.91 (d, J=7.6 Hz, 1H), 6.75 (d, J=8.3 Hz, 1H), 6.65 (d, J=7.8 Hz, 1H), 5.83 (d, J=7.6 Hz, 1H), 3.29 (s, 3H, CH3), 13C NMR (100 MHz, CDCl3) δ 175.62, 143.35, 141.62, 133.65, 132.99, 131.62, 129.56, 129.06, 128.90, 128.04, 126.54, 126.17, 125.43, 124.94, 124.73, 124.43, 123.73, 118.79, 116.11, 110.07, 100.70, 80.91, 79.62, 26.57.
Representative Peaks of Minor Isomer: 1H NMR δ 7.63-7.54 (m), 6.80 (d, J=8.4 Hz), 3.14 (s), 13C NMR δ: 143.15, 142.14, 136.12, 134.05, 133.25, 129.29, 128.69, 128.20, 126.74, 110.27, 100.85, 81.74, 80.31, 26.79. HRMS calculated [M+H]+ for C24H18O2N2Br: 445.0546. found: 445.0563. FTIR (cm-1) 3015, 2939, 1851, 1788, 1774, 1716, 1637, 1608, 1568, 1488, 1463, 1424, 1358, 1342, 1257, 1217, 1141, 1101, 1057, 1026, 954, 899, 812, 756, 713.

Example 9

1'-Methyl-4bH-spiro[benzo[4,5][1,3]oxazino[2,3-a]isoquinoline-6,3'-indolin]-2'-one (4b)

Following the general procedure, treatment of isoquinoline 1a (0.064 g, 59 µL, 0.50 mmol) and 1-methylindoline-2,3-dione (0.080 g, 0.50 mmol) with 2-(trimethylsilyl)phenyl trifluoromethane sulfonate 2a (0.223 g, 182 µL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 70° C. for 24 h followed by flash column chromatography (Pet. ether/EtOAc=93/07) of the crude reaction mixture afforded 1'-methyl-4bH-spiro[benzo[4,5][1,3]oxazino[2,3-a]isoquinoline-6,3'-indolin]-2'-one as inseparable mixture of diastereomers as a white solid (0.130 g, 71%, dr determined by 1H NMR analysis of crude reaction mixture is 4:1). Rf (Pet. ether/EtOAc=70/30): 0.57 1H NMR (400 MHz, CDC3) δ 7.50-7.47 (m, 2H), 7.43-7.35 (m, 3H), 7.32-7.30 (m, 1H), 7.28-7.27 (m, 1H), 7.24-7.16 (m, 2H), 7.08-6.90 (m, 3H), 6.83 (d, J=8.3 Hz, 1H), 6.69 (d, J=7.6 Hz, 1H), 5.87 (d, J=7.6 Hz, 1H), 3.33 (s, 3H, CH3), 13C NMR (100 MHz, CDC3) δ 176.11, 144.22, 141.60, 131.69, 131.61, 130.09, 129.30, 129.11, 128.89, 128.64, 126.62, 126.19, 125.09, 124.98, 124.81, 124.19, 123.61, 123.43, 118.45, 108.42, 100.57, 80.64, 79.76, 26.37. Representative Peaks of Minor Isomer: 1H NMR δ 7.54-7.53 (m), 6.65-6.60 (m), 5.89 (d, J=7.3 Hz), 3.18 (s), 13C NMR δ: 174.94, 130.32, 126.89, 126.74, 125.72, 124.49, 123.49, 118.28, 108.60, 100.44, 81.47, 26.60. HRMS calculated [M+H]+ for C24H19O2N2: 367.1441. found: 367.1438. FTIR (cm-1) 3062, 3011, 2961, 2933, 1949, 1719, 1659, 1630, 1613, 1567, 1488, 1471, 1458, 1418, 1433, 1369, 1345, 1300, 1274, 1250, 1216, 1170, 1157, 1130, 1025, 1001, 976, 953, 905, 877, 861, 753, 695, 665, 650, 623, 570.

Example 10

1'-Benzyl-4bH spiro[benzo[4,5][1,3]oxazino[2,3-a]isoquinoline-6,3'-indolin]-2'-one To a flame-dried screw-capped test tube equipped with a magnetic stir bar was added 18-crown-6 (0.198 g, 0.75 mmol), KF (potassium fluoride) (0.043 g, 0.75 mmol) and N-benzyl isatin (59.3 mg, 0.25 mmol). Then the screw-capped tube was evacuated and backfilled with argon. The mixture was dissolved in THF (tetrahydrofuran) (1.0 mL) under argon atmosphere. To the stirring solution was added the isoquinoline (32.3 mg, 30 µL, 0.25 mmol) and aryne precursor (111.9 mg, 91 µL, 0.375 mmol) and placed the reaction mixture in a preheated oil bath at 70° C. When TLC control showed the completion of the reaction (typically after 24 h), the reaction was stopped and the crude reaction mixture was purified by column chromatography on silica gel (10% EtOAc:Pet Ether) to afford the spiro-oxazino isoquinoline derivative I, 1'-Benzyl-4bH-spiro[benzo[4,5][1,3]oxazino[2,3-a]isoquinoline-6,3'-indolin]-2'-one in 78% (68 mg) yield.

$R_f$ (Pet. ether/EtOAc=80/20): 0.43 $^1$H NMR (400 MHz, CDCl$_3$) δ 8.16-8.06 (m, 2H, H$_{ar}$), 8.02-7.94 (m, 4H, H$_{ar}$), 7.90-7.81 (m, 4H, H$_{ar}$), 7.77-7.65 (m, 3H, H$_{ar}$), 7.52-7.34 (m, 4H, H$_{ar}$), 7.19 (d, J=19.9 Hz, 1H, H$_{ar}$), 7.09 (d, J=9.4 Hz, 1H, H$_{ar}$), 6.01 (d, J=9.4 Hz, 1H, H$_{olefinic}$), 5.18 (d, J=19.8 Hz, 1H, CH), 4.80 (d, J=19.8 Hz, 1H, CH). $^{13}$C NMR (100 MHz, CDCl$_3$) δ 176.29, 175.28, 143.44, 143.09, 142.13, 141.76, 135.81, 131.73, 130.16, 129.47, 129.20, 129.07, 129.02, 128.94, 128.83, 127.95, 127.57, 127.48, 126.75, 126.26, 126.14, 125.06, 125.03, 124.33, 123.74, 123.61, 118.62, 109.56, 100.68, 80.69, 79.83, 44.24, 43.96.

Example 10a

1'-Benzyl-4bH-spiro[benzo[4,5][1,3]oxazino[2,3-a]isoquinoline-6,3'-indolin]-2'-one (4c)

Following the general procedure, treatment of isoquinoline 1a (0.064 g, 59 µL, 0.50 mmol) and 1-benzylindoline-2,3-dione (0.119 g, 0.50 mmol) with 2-(trimethylsilyl)phenyl trifluoromethane sulfonate 2a (0.223 g, 182 µL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 70° C. for 24 h followed by flash column chromatography (Pet. ether/EtOAc=93/07) of the crude reaction mixture afforded 1'-benzyl-4bH-spiro[benzo[4,5][1,3]oxazino[2,3-a]isoquinoline-6,3'-indolin]-2'-one as inseparable mixture of diastereomers as a white solid (0.172 g, 77%, dr determined by 1H NMR analysis of crude reaction mixture is 6:1).

Rf (Pet. ether/EtOAc=70/30): 0.61 1H NMR (400 MHz, CDCl3) δ 7.55 (s, 1H), 7.47 (d, J=7.6 Hz, 1H), 7.43-7.36 (m, 4H), 7.33-7.29 (m, 4H), 7.23-7.19 (m, 1H), 7.17-7.14 (m, 2H), 7.02 (d, J=7.4 Hz, 1H), 6.99-6.95 (m, 1H), 6.94-6.89 (m, 2H), 6.76 (d, J=7.9 Hz, 1H), 6.69 (d, J=7.9 Hz, 1H), 5.82 (d, J=7.6 Hz, 1H), 5.16 (d, J=15.7 Hz, 1H), 4.85 (d, J=15.6 Hz, 1H). 13C NMR (100 MHz, CDCl3) δ 176.29, 143.44, 141.76, 135.81, 131.73, 130.16, 129.47, 129.20, 129.07, 129.02, 128.83, 127.95, 127.48, 126.75, 126.26, 126.14, 125.06, 125.03, 124.33, 123.74, 123.61, 118.62, 109.56, 100.68, 80.69, 79.83, 43.96. Representative Peaks of Minor Isomer: 1H NMR δ 7.51 (s), 7.11 (s), 7.06 (s), 6.82 (d, J=7.9 Hz), 6.66 (m), 5.87 (d, J=7.6 Hz), 5.04 (d, J=15.7 Hz), 4.66 (d, J=15.6 Hz). 13C NMR δ: 175.28, 143.09, 142.13, 130.27, 128.94, 128.66, 127.84, 127.57, 125.83, 124.64, 118.50, 109.78, 81.67, 44.24. HRMS calculated [M+H]+ for C30H23O2N2: 443.1754. found: 443.1756. FTIR (cm-1) 3065, 3018, 2927, 2401, 1715, 1614, 1489, 1468, 1434, 1346, 1291, 1216, 1174, 1102, 1078, 1044, 1029, 1009, 977, 756, 698, 668.

Example 11

1'-Allyl-4bH-spiro[benzo[4,5][1,3]oxazino[2,3-a]isoquinoline-6,3'-indolin]-2'-one (4d)

Following the general procedure, treatment of isoquinoline 1a (0.064 g, 59 µL, 0.50 mmol) and 1-allylindoline-2,3-dione (0.080 g, 0.50 mmol) with 2-(trimethylsilyl)phenyl trifluoromethane sulfonate 2a (0.223 g, 182 µL, 0.75 mmol) in the presence of KF (0.087 g, 1.50 mmol) and 18-crown-6 (0.396 g, 1.50 mmol) in THF (2.0 mL) at 70° C. for 24 h followed by flash column chromatography (Pet. ether/EtOAc=93/07) of the crude reaction mixture afforded 1'-allyl-4bH-spiro[benzo[4,5][1,3]oxazino[2,3-a]isoquinoline-6,3'-indolin]-2'-one as inseparable mixture of diastereomers as a white solid (0.119 g, 60%, dr determined by 1H NMR analysis of crude reaction mixture is 6:1). Rf (Pet. ether/EtOAc=70/30): 0.65 1H NMR (400 MHz, CDCl3) δ 7.52 (s, 1H), 7.47 (d, J=7.6 Hz, 1H), 7.38-7.32 (m, 3H), 7.30-7.15 (m, 3H), 7.05 (d, J=7.4 Hz, 1H), 7.02-6.93 (m, 3H), 6.90 (d, J=7.9 Hz, 1H), 6.72 (d, J=8.1 Hz, 1H), 6.03-5.93 (m, 1H), 5.84 (d, J=7.6 Hz, 1H), 5.43-5.33 (m, 2H), 4.57-4.51 (m, 1H), 4.43-4.35 (m, 1H). 13C NMR (100 MHz, CDC3) δ 175.99, 143.52, 141.72, 131.76, 131.71, 131.29, 130.07, 129.41, 129.17, 128.96, 128.77, 126.69, 126.09, 125.08, 125.01, 124.60, 124.29, 123.64, 123.55, 118.54, 118.05, 109.41, 100.66, 80.68, 79.77, 42.49. Representative Peaks of Minor Isomer: 1H NMR δ 7.55 (d, J=7.6 Hz), 7.44-7.40 (m), 6.68 (d, J=8.2 Hz), 5.29-5.25 (m), 4.26-4.20 (m). 13C NMR δ: 175.89, 143.24, 130.26, 128.69, 126.24, 125.79, 118.43, 109.64, 100.56, 81.61, 42.78. HRMS calculated [M+H]+ for C26H21O2N2: 393.1598. found: 393.1596. FTIR (cm-1) 2925, 2856, 1716, 1612, 1488, 1466, 1354, 1285, 1196, 1175, 1101, 1023, 999, 933, 750, 692, 598.

Example 12

1'-Phenyl-4bH-spiro[benzo[4,5][1,3]oxazino[2,3-a]isoquinoline-6,3'-indolin]-2'-one (4e)

Following the general procedure, treatment of isoquinoline 1a (0.064 g, 59 µL, 0.50 mmol) and 1-phenylindoline-2,3-dione (0.112 g, 0.50 mmol) with 2-(trimethylsilyl)phenyl trifluoromethane sulfonate 2a (0.223 g, 182 µL, 0.75 mmol) in the presence of KF (0.087 g, 1.50 mmol) and 1,4,7,10,13,16-hexaoxacyclooctadecane (0.396 g, 1.50 mmol) in THE (2.0 mL) at 70° C. for 24 h followed by flash column chromatography (Pet. ether/EtOAc=95/05) of the crude reaction mixture afforded 1'-phenyl-4bHspiro[benzo[4,5][1,3]oxazino[2,3-a]isoquinoline-6,3'-indolin]-2'-one as inseparable mixture of diastereomers as a white solid (0.147 g, 69%, dr determined by 1H NMR analysis of crude reaction mixture is 4:1).

Rf (Pet. ether/EtOAc=70/30): 0.71 1H NMR (400 MHz, CDCl3) δ 7.63-7.45 (m, 8H), 7.40-7.34 (m, 3H), 7.29-7.19 (m, 3H), 7.13 (d, J=7.1 Hz, 1H), 7.06-6.98 (m, 3H), 6.92 (d, J=5.5 Hz, 1H), 5.88 (d, J=7.4 Hz, 1H). 13C NMR (100 MHz, CDCl3) δ 175.47, 144.16, 141.65, 134.13, 131.66, 131.54, 130.01, 129.80, 129.43, 129.22, 128.95, 128.83, 128.35, 126.93, 126.69, 126.54, 126.47, 126.10, 125.25, 124.99, 124.28, 124.12, 123.67, 118.68, 109.83, 100.74, 80.85, 79.79. Representative Peaks of Minor Isomer: 13C NMR δ: 174.17, 143.93, 142.20, 129.55, 129.47, 129.35, 128.74, 126.63, 126.05, 125.80, 124.63, 124.06, 123.73, 118.57, 109.98, 100.57, 81.71, 81.41. HRMS calculated [M+H]+ for C29H21O2N2: 429.1598. found: 429.1607. FTIR (cm-1) 2928, 1728, 1657, 1629, 1481, 1454, 1429, 1363, 1303, 1248, 1201, 1168, 1100, 1026, 932, 746, 696.

Example 13

5'-Methoxy-1'-methyl-4bH-spiro[benzo[4,5][1,3]oxazino[2,3-a]isoquinoline-6,3' indolin]-2'-one (4f)

Following the general procedure, treatment of isoquinoline 1a (0.064 g, 59 µL, 0.50 mmol) and 5-methoxy-1-methylindoline-2,3-dione (0.096 g, 0.50 mmol) with 2-(trimethylsilyl)phenyl trifluoromethane sulfonate 2a (0.223 g, 182 µL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 70° C. for 24 h followed by flash column chromatography (Pet. ether/EtOAc=85/15) of the crude reaction mixture afforded 5'-methoxy-1'-methyl-4bH-spiro[benzo[4,5][1,3]oxazino[2,3-a]isoquinoline-6,3'-indolin]-2'-one as inseparable mixture of diastereomers as a white solid (0.143 g, 72%, dr determined by 1H NMR analysis of crude reaction mixture is 5:1).

Rf (Pet. ether/EtOAc=70/30): 0.46 1H NMR (500 MHz, CDCl3) δ 7.53-7.49 (m, 2H), 7.33 (s, 3H), 7.22-7.17 (m, 2H), 6.98-6.94 (m, 2H), 6.82 (d, J=11.3 Hz, 2H), 6.71-6.64 (m, 2H), 5.83 (d, J=6.8 Hz, 1H), 3.68 (s, 3H, CH3), 3.31 (s, 3H, CH3). 13C NMR (125 MHz, CDCl3) δ 176.03, 156.75, 141.57, 137.63, 132.81, 131.69, 129.39, 129.20, 128.90, 128.73, 126.71, 126.18, 126.06, 125.06, 124.26, 123.51, 118.45, 115.11, 111.58, 109.05, 100.59, 80.74, 80.21, 55.87, 26.51. Representative Peaks of Minor Isomer: 1H NMR δ 3.85 (s), 3.17 (s). 13C NMR δ: 174.79, 156.69, 142.07, 137.50, 133.51, 131.93, 129.96, 126.83, 129.79, 125.69, 124.70, 124.57, 123.58, 118.35, 114.19, 112.74, 109.00, 100.50, 81.54, 80.92, 56.01, 26.75. HRMS calculated [M+H]+ for C25H21O3N2: 397.1547. found: 397.1554. FTIR (cm-1) 2868, 1695, 1637, 1602, 1490, 1451, 1349, 1286, 1206, 1163, 1105, 1031, 949, 837, 754, 702.

Example 14

5'-Chloro-1'-methyl-4bH-spiro[benzo[4,5][1,3]oxazino[2,3-a]isoquinoline-6,3'-indolin]-2'-one (4g)

Following the general procedure, treatment of isoquinoline 1a (0.064 g, 59 µL, 0.50 mmol) and 5-chloro-1-methylindoline-2,3-dione (0.098 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 70° C. for 24 h followed by flash column chromatography (Pet. ether/EtOAc=93/07) of the crude reaction mixture afforded 5'-chloro-1'-methyl-4bH-spiro[benzo[4,5][1,3]oxazino[2,3-a]isoquinoline-6,3'-indolin]-2'-one as inseparable mixture of diastereomers as a white solid (0.162 g, 81%, dr determined by 1H NMR analysis of crude reaction mixture is 5:1).

Rf (Pet. ether/EtOAc=70/30): 0.58 1H NMR (400 MHz, CDCl3) δ 7.45-7.42 (m, 2H), 7.33-7.30 (m, 2H), 7.27-7.25 (m, 1H), 7.21 (d, J=2.2 Hz, 1H), 7.19-7.11 (m, 2H), 7.04-6.85 (m, 3H), 6.78 (d, J=8.2 Hz, 1H), 6.64 (d, J=7.7 Hz, 1H), 5.82 (d, J=7.7 Hz, 1H), 3.28 (s, 3H, CH3), 13C NMR (100 MHz, CDCl3) δ 200.32, 159.22, 157.69, 147.32, 145.21, 143.28, 142.62, 142.07, 141.99, 141.91, 141.81, 138.83, 138.39, 137.33, 136.61, 136.53, 136.20, 135.32, 129.15, 117.67, 106.76, 81.83, 80.29, 13.96. Representative Peaks of Minor Isomer: 1H NMR δ 7.50-7.49 (m), 7.38-7.36 (m), 6.63-6.55 (m), 5.84 (d, J=7.3 Hz), 3.13 (s), 13C NMR δ: 198.93, 158.98, 158.34, 147.78, 143.58, 142.27, 141.52, 139.03, 137.90, 137.51, 136.53, 128.96, 117.86, 106.55, 82.85, 81.15, 14.23. HRMS calculated [M+H]+ for $C_{24}H_{18}O_2N_2Cl$: 401.1051. found: 401.1051. FTIR (cm-1) 2956, 2933, 2873, 1723, 1637, 1610, 1488, 1460, 1432, 1360, 1340, 1312, 1251, 1103,1025, 955, 812, 769, 725, 692.

Example 15

5'-fluoro-1'-methyl-4bH-spiro[benzo[4,5][1,3]oxazino[2,3-a]isoquinoline-6,3'-indolin]-2'-one (4h)

Following the general procedure, treatment of isoquinoline 1a (0.064 g, 59 μL, 0.50 mmol) and 5-fluoro-1-methylindoline-2,3-dione (0.090 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane 0.396 g, 1.50 mmol) in THF (2.0 mL) at 70° C. for 24 h followed by flash column chromatography (Pet. ether/EtOAc=93/07) of the crude reaction mixture afforded 5'-fluoro-1'-methyl-4bH-spiro[benzo[4,5][1,3]oxazino[2,3-a]isoquinoline-6,3'-indolin]-2'-one as inseparable mixture of diastereomers as a white solid (0.134 g, 69%, dr determined by 1H NMR analysis of crude reaction mixture is 6:1).

Rf (Pet. ether/EtOAc=70/30): 0.59 1H NMR (200 MHz, CDCl3) δ 7.48-7.45 (m, 2H), 7.38-7.21 (m, 3H), 7.24-7.11 (m, 2H), 7.04-6.90 (m, 3H), 6.83-6.75 (m, 2H), 6.67 (d, J=7.6 Hz, 1H), 5.83 (d, J=7.6 Hz, 1H), 3.31 (s, 3H, CH3), 13C NMR (50 MHz, CDCl3) δ 176.70, 159.75 (d, J=244.0 Hz), 141.63, 140.21, 136.12, 133.33 (d, J=8.3 Hz), 131.66, 129.53, 129.14, 129.01, 126.54, 126.17, 125.7 (d, J=15.2 Hz), 124.83, 124.40, 123.68, 118.74, 116.44 (d, J=23.8 Hz), 112.98 (d, J=25.3 Hz), 109.2 (d, J=8.1 Hz), 100.88, 80.92, 79.88, 26.51. Representative Peaks of Minor. Isomer: 1H NMR δ 6.63-6.56 (m), 5.88-5.85 (m), 3.16 (s), 13C NMR δ: 175.97, 160.01, 129.24, 128.90, 128.70, 126.09, 26.82. HRMS calculated [M+H]+ for C24H18O2N2F: 385.1347. found: 385.1347. FTIR (cm-1) 2926, 2729, 1735, 1604, 1460, 1377, 1353, 1299, 1251, 1269, 1215, 1123, 1038, 990, 950, 760, 723.

Example 16

1',8,9-Trimethyl-4bH-spiro[benzo[4,5][1,3]oxazino[2,3-a]isoquinoline-6,3'-indolin]-2'-one (4i)

Following the general procedure, treatment of isoquinoline 1a (0.032 g, 30 μL, 0.25 mmol) and 1-methylindoline-2,3-dione (0.040 g, 0.25 mmol) with 4,5-dimethyl-2-(trimethylsilyl)phenyl trifluoromethane sulfonate 2b (0.122 g, 0.375 mmol) in the presence of KF (0.043 g, 0.75 mmol) and 1,4,7,10,13,16-hexaoxacyclooctadecane (0.198 g, 0.75 mmol) in THF (1.0 mL) at 70° C. for 24 h followed by flash column chromatography (Pet. ether/EtOAc=93/07) of the crude reaction mixture afforded 1',8,9-trimethyl-4bHspiro[benzo[4,5][1,3]oxazino[2,3-a]isoquinoline-6,3'-indolin]-2'-one as inseparable mixture of diastereomers as a white solid (0.074 g, 74%, dr determined by 1H NMR analysis of crude reaction mixture is 6:1).

Rf (Pet. ether/EtOAc=70/30): 0.55 1H NMR (200 MHz, CDCl3) δ 7.51-7.47 (m, 2H), 7.37-7.24 (m, 2H), 7.21-7.13 (m, 3H), 7.09-6.98 (m, 2H), 6.95-6.89 (m, 2H), 6.43 (s, 1H), 5.81 (d, J=7.7 Hz, 1H), 3.35 (s, 3H, CH3), 2.31 (s, 3H, CH3), 2.13 (s, 3H, CH3). 13C NMR (50 MHz, CDCl3) δ 176.39, 144.37, 139.62, 137.64, 132.29, 131.97, 131.89, 130.03, 129.51, 129.29, 129.22, 127.02, 125.89, 125.06, 124.91, 124.18, 123.63, 119.67, 108.44, 100.08, 80.75, 79.65, 26.44, 19.97, 19.28. Representative Peaks of Minor Isomer: 1H NMR δ 7.55 (d, J=7.5 Hz), 7.44-7.43 (m), 6.66 (s), 5.87-5.79 (m), 3.22 (s), 13C NMR δ: 175.31, 144.13, 140.02, 137.96, 132.60, 130.26, 128.70, 127.22, 125.63, 124.47, 123.51, 119.35, 108.62, 81.56, 80.48, 26.06. HRMS calculated [M+H]+ for C26H23O2N2: 395.1754. found: 395.1758. FTIR (cm-1) 2869, 1719, 1612, 1565, 1492, 1470, 1352, 1298, 1252, 1119, 1043, 990, 947, 858, 846, 757.

Example 17

1-Methyl-4b'H-spiro[indoline-3,6'-[1,3]dioxolo[4",5":4',5']benzo[1',2':4,5][1,3]oxazino[2,3-a]isoquinolin]-2-one (4j)

Following the general procedure, treatment of isoquinoline 1a (0.032 g, 30 μL, 0.25 mmol) and 1-methylindoline-2,3-dione (0.040 g, 0.25 mmol) with 6-(trimethylsilyl)benzo[d][1,3]dioxol-5-yl trifluoromethane sulfonate 2c (0.128 g, 0.375 mmol) in the presence of KF (0.043g, 0.75 mmol) and 1,4,7,10,13,16-hexaoxacyclooctadecane (0.198 g, 0.75 mmol) in THF (1.0 mL) at 70° C. for 24 h followed by flash column chromatography (Pet. Ether/EtOAc=90/10) of the crude reaction mixture afforded 1-methyl-4b'H-spiro[indoline-3,6'-[1,3]dioxolo[4",5":4',5']benzo[1',2':4,5][1,3]oxazino[2,3-a]isoquinolin]-2-one as inseparable mixture of diastereomers as a yellow solid (0.069 g, 67%, dr determined by 1H NMR analysis of crude reaction mixture is 10:1).

Rf (Pet. ether/EtOAc=70/30): 0.48 1H NMR (500 MHz, CDCl3) δ 7.45 (d, J=7.7 Hz, 1H), 7.37 (s, 1H), 7.32-7.29 (m, 2H), 7.20 (t, J=7.0 Hz, 1H), 7.14 (d, J=7.7 Hz, 1H), 7.04 (d, J=7.2 Hz, 1H), 6.98 (t, J=7.0 Hz, 1H), 6.87 (d, J=7.8 Hz, 1H), 6.81-6.79 (m, 2H), 6.09 (s, 1H), 5.92 (d, J=9.6 Hz, 2H), 5.82 (d, J=7.6 Hz, 1H), 3.31 (s, 3H, CH3), 13C NMR (1125 MHz, CDCl3) δ 176.01, 148.15, 144.46, 144.10, 136.51, 131.79, 130.11, 129.42, 129.29, 129.11, 125.97, 124.85, 124.68, 124.18, 123.60, 118.83, 108.48, 105.35, 101.47, 100.63, 100.14, 80.81, 79.51, 26.34. Representative Peaks of Minor Isomer: 1H NMR δ 7.55-7.54 (m), 6.93-6.91 (m), 6.07-6.06 (m), 5.87-5.86 (m), 3.17 (s), 13C NMR δ: 131.53, 130.35, 129.50, 129.36, 129.22, 128.57, 125.69, 124.75, 124.51, 123.53, 108.61, 106.50, 100.05, 26.56. HRMS calculated [M+H]+ for C25H19O2N2: 411.1339. found: 411.1339. FTIR (cm-1) 2926, 1778, 1716, 1614, 1492, 1470, 1369, 1349, 1292, 1215, 1091, 1026, 977, 954, 900, 752, 667.

Example 18

8,9-Difluoro-1'-methyl-4bH-spiro[benzo[4,5][1,3]oxazino[2,3-a]isoquinoline-6,3' indolin]-2'-one (4k)

Following the general procedure, treatment of isoquinoline 1a (0.032 g, 30 μL, 0.25 mmol) and 1-methylindoline-2,3-dione (0.040 g, 0.25 mmol) with 4,5-difluoro-2-(trimethylsilyl)phenyl trifluoromethanesulfonate 2d (0.125 g, 0.375 mmol) in the presence of KF (0.043g, 0.75 mmol) and 1,4,7,10,13,16-hexaoxacyclooctadecane (0.198 g, 0.75 mmol) in THF (1.0 mL) at 70° C. for 24 h followed by flash column chromatography (Pet. ether/EtOAc=93/07) of the crude reaction mixture afforded 8,9-difluoro-1'-methyl-4bH-spiro[benzo[4,5][1,3]oxazino[2,3-a]isoquinoline-6,3'-indolin]-2'-one as inseparable mixture of diastereomers as a yellow solid (0.070 g, 70%, dr determined by 1H NMR analysis of crude reaction mixture is 12:1).

Rf (Pet. ether/EtOAc=70/30): 0.59 1H NMR (400 MHz, CDCl3) δ 7.42 (t, J=8.8 Hz, 2H), 7.33-7.28 (m, 3H), 7.21-7.11 (m, 3H), 6.99-6.96 (m, 1H), 6.91 (d, J=7.7 Hz, 1H), 6.75 (d, J=7.9 Hz, 1H), 6.65 (d, J=8.2 Hz, 1H), 5.83 (d, J=7.6 Hz, 1H), 3.29 (s, 3H, CH3), 13C NMR (100 MHz, CDCl3) δ 176.70, 159.75 (dd, J1=12.1 Hz, J2=244.0 Hz), 159.64 (dd, J1=11.0 Hz, J2=240.7 Hz), 141.63, 140.21, 136.12, 133.33 (d, J=8.3 Hz), 131.66, 129.53, 129.01 (m), 126.54, 126.17, 125.7 (d, J=15.2 Hz), 124.83, 124.40, 123.68, 118.74, 116.44 (d, J=23.8 Hz), 112.98 (d, J=25.3 Hz), 109.2 (d, J=8.1 Hz), 100.88, 80.92, 79.88, 26.51. Representative Peaks of Minor Isomer: 1H NMR δ 7.62-7.55 (m), 6.81-6.79 (m), 3.14 (s), 13C NMR δ: 174.94, 130.32, 126.89, 126.74, 125.72, 124.49, 123.49, 118.28, 108.60, 100.44, 81.47, 26.60. HRMS calculated [M+H]+ for C24H17O2N2F2: 403.1253. found: 403.1253. FTIR (cm-1) 3015, 2928, 1722, 1636, 1607, 1585, 1488, 1460, 1428, 1358, 1339, 1311, 1250, 1101, 1056, 1025, 1001, 953, 859, 811, 755, 665.

Example 19

1-Methyl-13b'H-spiro[indoline-3,15'-naphtho[2',1':4,5][1,3]oxazino[2,3-a]isoquinolin]-2-one (4l)

Following the general procedure, treatment of isoquinoline 1a (0.032 g, 30 μL, 0.25 mmol) and 1-methylindoline-2,3-dione (0.040 g, 0.25 mmol) with 2-(trimethylsilyl)naphthalen-1-yl trifluoromethanesulfonate 2e (0.131 g, 0.375 mmol) in the presence of KF (0.043 g, 0.75 mmol) and 1,4,7,10,13,16-hexaoxacyclooctadecane (0.198 g, 0.75 mmol) in THF (1.0 mL) at 70° C. for 24 h followed by flash column chromatography (Pet. ether/EtOAc=90/10) of the crude reaction mixture afforded 1-methyl-13b'H-spiro[indoline-3,15'-naphtho[2',1':4,5][1,3]oxazino[2,3-a]isoquinolin]-2-one as inseparable mixture of diastereomers as a white solid (0.079 g, 76%, dr determined by 1H NMR analysis of crude reaction mixture is 6:1).

Rf (Pet. ether/EtOAc=70/30): 0.50 1H NMR (400 MHz, CDCl3) δ 7.88 (d, J=9.1 Hz, 1H), 7.78 (d, J=8.0 Hz, 1H), 7.55 (d, J=8.9 Hz, 2H), 7.41 (d, J=7.6 Hz, 1H), 7.31-7.26 (m, 2H), 7.24 (m, 1H), 7.20 (t, J=7.2 Hz, 2H), 7.13 (d, J=7.9 Hz, 1H), 7.07 (d, J=7.6 Hz, 1H), 6.94 (d, J=7.7 Hz, 2H), 6.83-6.79 (m, 2H), 5.86 (d, J=7.7 Hz, 1H), 3.45 (s, 3H, CH3), 13C NMR (100 MHz, CDCl3) δ 175.00, 144.51, 140.72, 131.55, 131.19, 130.91, 130.60, 130.48, 130.34, 129.31, 129.17, 127.63, 126.98, 124.60, 124.19, 123.77, 122.50, 118.30, 112.16, 108.93, 98.32, 79.37, 78.14, 26.66. Representative Peaks of Minor Isomer: 1H NMR δ 7.97 (t, J=7.8 Hz), 7.83 (d, J=7.8 Hz), 7.51-7.48 (m), 7.04-7.02 (m), 6.88-6.85 (m), 6.02 (d, J=7.7 Hz), 3.31 (s), 13C NMR δ: 129.79, 127.34, 123.28, 118.54, 111.71, 109.11, 78.96, 77.37, 26.92. HRMS calculated [M+H]+ for C28H21O2N2: 417.1598. found: 417.1603. FTIR (cm-1) 2925, 2859, 1722, 1611, 1563, 1490, 1471, 1420, 1368, 1351, 1296, 1253, 1113, 1091, 1022, 992, 941, 814, 753, 665.

Example 20

1-Bromo-1'-methyl-4bH-spiro[benzo[4,5][1,3]oxazino[2,3-a]isoquinoline-6,3'-indolin]2'-one (4m)

Following the general procedure, treatment of 5-bromoisoquinoline 1m (0.104 g, 0.5 mmol) and 1-methylindoline-2,3-dione (0.080 g, 0.5 mmol) with 2-(trimethylsilyl)phenyl trifluoromethane sulfonate 2a (0.223 g, 182 μL, 0.75 mmol) in the presence of KF (0.087 g, 1.5 mmol) and 1,4,7,10,13,16-hexaoxacyclooctadecane (0.396 g, 1.5 mmol) in THF (2.0 mL) at 70° C. for 24 h followed by flash column chromatography (Pet. ether I/EtOAc=90/10) of the crude reaction mixture afforded 1-bromo-1'-methyl-4bH-spiro[benzo[4,5][1,3]oxazino[2,3-a]isoquinoline-6,3'-indolin]-2'-one as a white solid (0.201 g, 90%, dr determined by 1H NMR analysis of crude reaction mixture is >20:1).

Rf (Pet. ether/EtOAc=70/30): 0.53 1H NMR (400 MHz, CDCl3) δ 7.54 (d, J=8.0 Hz, 1H), 7.47 (s, 1H), 7.41 (d, J=7.7 Hz, 1H), 7.35-7.25 (m, 3H), 7.09-6.93 (m, 5H), 6.89 (d, J=7.8 Hz, 1H), 6.68 (d, J=7.8 Hz, 1H), 6.16 (d, J=7.7 Hz, 1H), 3.32 (s, 3H, CH3), 13C NMR (100 MHz, CDCl3) δ 176.01, 144.23, 141.06, 133.32, 131.40, 131.34, 130.84, 130.33, 128.89, 128.60, 126.74, 126.71, 126.62, 126.41, 124.85, 124.02, 123.80, 119.41, 118.69, 108.61, 98.98, 80.30, 79.87, 26.48. HRMS calculated [M+H]+ for C24H18O2N2Br: 445.0546. found: 445.0546. FTIR (cm-1) 2867, 1956, 1716, 1634, 1611, 1566, 1488, 1470, 1352, 1299, 1251, 1112, 991, 946, 755, 692.

Example 21

1'-Methyl-6aH-spiro[benzo[4,5][1,3]oxazino[3,2-a]quinoline-5,3'-indolin]-2'-one (4n)

Following the general procedure, treatment of quinoline (0.064 g, 59 μL, 0.50 mmol) and 1-methylindoline-2,3-dione (0.080 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and (1,4,7,10,13,16-hexaoxacyclooctadecane 0.396 g, 1.50 mmol) in THF (2.0 mL) at 70° C. for 24 h followed by flash column chromatography (Pet. ether/EtOAc=70/30) of the crude reaction mixture afforded 1'-methyl-6aH-spiro[benzo[4,5][1,3]oxazino[3,2-a]quinoline-5,3'-indolin]-2'-one as a red solid (0.089 g, 49%, dr determined by 1H NMR analysis of crude reaction mixture is >20:1).

Rf (Pet. ether/EtOAc=70/30): 0.31 1H NMR (400 MHz, CDCl3) δ 7.62 (d, J=8.2 Hz, 1H), 7.39-7.34 (m, 2H), 7.30-7.24 (m, 3H), 7.11 (t, J=7.6 Hz, 1H), 6.98-6.81 (m, 6H), 6.59 (d, J=5.0 Hz, 1H), 6.05-6.02 (m, 1H), 3.30 (s, 3H, CH3), 13C NMR (100 MHz, CDCl3) δ 175.95, 144.10, 140.30, 139.59, 131.66, 130.28, 130.16, 129.94, 129.46, 128.50, 127.49, 126.95, 125.65, 125.59, 124.63, 123.72, 121.28, 120.08, 117.84, 112.84, 108.63, 80.07, 79.32, 26.43. HRMS calculated [M+H]+ for C24H19O2N2: 367.1441. found: 367.1441. FTIR (cm-1) 2959, 2872, 1716, 1636, 1611, 1567, 1488, 1466, 1359, 1251, 1102, 1024, 814, 754.

Example 22

1'-Benzyl-6aH-spiro[benzo[4,5][1,3]oxazino[3,2-a]quinoline-5,3'-indolin]-2'-one (4o)

Following the general procedure, treatment of quinoline (0.129 g, 118 μL, 1.0 mmol) and 1-benzylindoline-2,3-dione (0.119 g, 0.50 mmol) with 2-(trimethylsilyl)phenyl trifluoromethane sulfonate 2a (0.298 g, 239 μL, 1.0 mmol) in the presence of KF (0.116 g, 2.0 mmol) and 1,4,7,10,13,16-hexaoxacyclooctadecane (0.528 g, 2.0 mmol) in THF (2.0 mL) at 70° C. for 24 h followed by flash column chromatography (Pet. ether/EtOAc=70/30) of the crude reaction mixture afforded 1'-benzyl-6aHspiro[benzo[4,5][1,3]oxazino[3,2-a]quinoline-5,3'-indolin]-2'-one as a yellow solid (0.139 g, 63% yield, dr determined by 1H NMR analysis of crude reaction mixture is >20:1).

Rf (Pet. ether/EtOAc=70/30): 0.36 1H NMR (500 MHz, CDCl3)_7.77 (d, J=8.0 Hz, 1H), 7.56-7.45 (m, 6H), 7.42-7.38 (m, 3H), 7.30-7.24 (m, 2H), 7.12-7.06 (m, 2H), 6.99-6.96 (m, 3H), 6.89 (d, J=7.8 Hz, 1H), 6.77 (d, J=5.1 Hz, 1H), 6.24-6.21 (m, 1H), 5.24 (d, J=15.5 Hz, 1H), 4.99 (d, J=15.5 Hz, 1H). 13C NMR (125 MHz, CDCl3) 176.11, 143.24, 140.37, 139.65, 135.76, 131.77, 130.45, 130.04, 130.00, 129.48, 129.07, 128.52, 127.96, 127.56, 127.54, 126.93, 125.77, 125.69, 124.72, 123.74, 121.34, 120.14, 117.91, 112.89, 109.69, 80.05, 79.45, 44.05. HRMS calculated [M+H]+ for C30H23O2N2: 443.1754. found: 443.1757. FTIR (cm-1) 3058, 2855, 1728, 1644, 1610, 1489, 1466, 1433, 1356, 1241, 1210, 1176, 1105, 1026, 992, 929, 751, 694.

Example 23

6-Phenyl-6-(trifluoromethyl)-4bH,6H-benzo[4,5][1,3]oxazino[2,3-a]isoquinoline (4p)

Following the general procedure, treatment of isoquinoline 1a (0.064 g, 59 μL, 0.50 mmol) and 2,2,2-trifluoro-1-phenylethan-1-one (0.087g, 70 μL, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 70° C. for 24 h followed by flash column chromatography (Pet. ether/EtOAc=97/03) of the crude reaction mixture afforded 6-phenyl-6-(trifluoromethyl)-4bH,6Hbenzo[4,5][1,3]oxazino[2,3-a]isoquinoline as inseparable mixture of diastereomers as a white solid (0.140 g, 74%, dr determined by 1H NMR analysis of crude reaction mixture is 5:1).

Rf (Pet. ether/EtOAc=70/30): 0.85 1H NMR (400 MHz, CDCl3) δ 7.87 (d, J=7.7 Hz, 2H), 7.67 (d, J=8.2 Hz, 1H), 7.56-7.49 (m, 3H), 7.38-7.33 (m, 2H), 7.29-7.19 (m, 3H), 7.14 (t, J=7.4 Hz, 2H), 6.87 (d, J=7.6 Hz, 1H), 6.05 (s, 1H), 5.80 (d, J=7.6 Hz, 1H). 13C NMR (100 MHz, CDCl3) δ 142.38, 137.77, 131.72, 129.88, 129.64, 129.49, 129.38, 129.10, 128.86, 128.65, 128.37, 127.10-127.03 (m), 124.65, 124.48, 122.41, 122.08, 118.37, 101.01, 82.96-82.10 (m), 79.60. Representative Peaks of Minor Isomer: 1H NMR δ 7.62 (d, J=8.7 Hz), 7.56-7.54 (m, 2H), 7.44-7.40 (m), 6.83 (d, J=7.6 Hz), 6.08 (s), 5.85 (d, J=7.6 Hz). 13C NMR δ: 141.89, 139.42, 131.44; 129.22, 128.94, 128.81, 124.74, 123.84, 123.45, 119.44, 100.89, 81.50. HRMS calculated [M+H]+ for C23H17ONF3: 380.1257. found 380.1262. FTIR (cm-1) 3016, 2871, 1700, 1646, 1599, 1490, 1454, 1355, 1287, 1248, 1171, 1117, 1039, 952, 756.

Example 24

Synthesis and Characterization of Indolin 2-Ones

1-Methyl-3-phenoxy-3-(pyridin-2-yl)indolin-2-one (8a)

Following the general procedure, treatment of pyridine 7a (0.060 g, 60 μL, 0.75 mmol) and 1-methylindoline-2,3-dione (0.080 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=65/35) of the crude reaction mixture afforded 1-methyl-3-phenoxy-3-(pyridin-2-yl)indolin-2-one 8a as a yellow solid (0.124 g, 79%). CCDCCCDC-938922 (8a), contains the supplementary crystallographic data for this paper.

Rf (Pet. ether/EtOAc=50/50): 0.61; 1H NMR (400 MHz, CDCl3) δ 8.49-8.47 (m, 1H), 8.17 (d, J=7.8 Hz, 1H), 7.84 (dt, J1=1.7 Hz, J2=7.8 Hz, J3=15.6 Hz, 1H), 7.34-7.29 (m, 1H), 7.24-7.22 (m, 2H), 7.16-7.11 (m, 2H), 7.05-6.96 (m, 2H), 6.90-6.85 (m, 3H), 3.26 (s, 3H, CH3). 13C NMR (100 MHz, CDCl3) δ 174.27, 159.00, 155.18, 149.34, 144.47, 137.18, 130.35, 129.21, 128.68, 125.50, 123.71, 123.19, 123.11, 121.07, 120.78, 108.93, 86.22, 26.65. HRMS calculated [M+H]+ for C20H17O2N2: 317.1285. found: 317.1282. FTIR (cm-1) 3058, 2926, 2855, 1729, 1611, 1588, 1491, 1471, 1434, 1369, 1348, 1302, 1239, 1214, 1157, 1131, 1108, 1091, 1032, 1051, 993, 972, 783, 694, 648, 618, 594.

Example 25

1-Benzyl-3-phenoxy-3-(pyridin-2-yl)indolin-2-one (8b)

Following the general procedure, treatment of pyridine 7a (0.060 g, 60 μL, 0.75 mmol) and 1-benzylindoline-2,3-dione (0.119 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=70/30) of the crude reaction mixture afforded benzyl-3-phenoxy-3-(pyridin-2-yl)indolin-2-one 8b as a yellow solid (0.145 g, 74%).

Rf (Pet. ether/EtOAc=50/50): 0.65; 1H NMR (400 MHz, CDCl3) δ 8.51-8.50 (m, 1H), 8.20 (d, J=8.0 Hz, 1H), 7.87 (dt, J1=1.7 Hz, J2=7.9 Hz, J3=15.6 Hz, 1H), 7.29-7.18 (m, 6H), 7.17-7.12 (m, 2H), 7.07-6.99 (m, 4H), 6.93 (d, J=7.9 Hz, 2H), 6.65 (d, J=7.8 Hz, 1H), 5.13 (d, J=15.9 Hz, 1H), 4.80 (d, J=15.9 Hz, 1H). 13C NMR (100 MHz, CDCl3) δ 174.02, 159.19, 155.06, 149.36, 143.60, 137.26, 135.10, 130.26, 129.34, 128.96, 128.75, 127.52, 127.26, 125.49, 124.10, 123.13, 123.12, 121.77, 120.95, 110.12, 86.71, 44.04. HRMS calculated [M+H]+ for C26H21O2N2: 393.1598. found: 393.1592. FTIR (cm-1) 3059, 2923, 2854,

Example 26

1-Allyl-3-phenoxy-3-(pyridin-2-yl)indolin-2-one (8c)

Following the general procedure, treatment of pyridine 7a (0.060 g, 60 μL, 0.75 mmol) and 1-allylindoline-2,3-dione (0.094 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=75/25) of the crude reaction mixture afforded 1-allyl-3-phenoxy-3-(pyridin-2-yl)indolin-2-one 8c as a yellow solid (0.126 g, 73%).

Rf (Pet. ether/EtOAc=50/50): 0.67; 1H NMR (400 MHz, CDC3) δ 8.53-8.52 (m, 1H), 8.22 (d, J=8.0 Hz, 1H), 7.89 (dt, J1=1.7 Hz, J2=7.8 Hz, J3=15.6 Hz, 1H), 7.35-7.26 (m, 3H), 7.19 (t, J=7.7 Hz, 2H), 7.10-7.02 (m, 2H), 6.99-6.97 (m, 2H), 6.85 (d, J=7.8 Hz, 1H), 5.79-5.69 (m, 1H), 5.16 (d, J=10.7 Hz, 1H), 5.08 (d, J=17.2 Hz, 1H), 4.55-4.50 (m, 1H), 4.35-4.29 (m, 1H). 13C NMR (100 MHz, CDC3) δ 173.84, 159.05, 155.07, 149.37, 143.75, 137.19, 130.61, 130.23, 129.20, 128.88, 125.59, 124.05, 123.18, 123.04, 121.64, 121.00, 117.65, 109.89, 86.59, 42.51. HRMS calculated [M+H]+ for C22H19O2N2: 343.1441. found: 343.1440. FTIR (cm-1) 3057, 3010, 2924, 2855, 1731, 1612, 1588, 1490, 1466, 1435, 1376, 1356, 1241, 1215, 1176, 1151, 1115, 755, 666.

Example 27

3-Phenoxy-1-phenyl-3-(pyridin-2-yl)indolin-2-one (8d)

Following the general procedure, treatment of pyridine 7a (0.060 g, 60 μL, 0.75 mmol) and 1-phenylindoline-2,3-dione (0.112 g, 0.50 mmol) with N 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=80/20) of the crude reaction mixture afforded 3-phenoxy-1-phenyl-3-(pyridin-2-yl)indolin-2-one 8d as a red solid (0.075 g, NMR yield 69%).

Rf (Pet. ether/EtOAc=50/50): 0.75; 1H NMR (400 MHz, CDCl3) δ 8.55-8.54 (m, 1H), 8.23 (d, J=7.9 Hz, 1H), 7.87 (dt, J1=1.8 Hz, J2=7.8 Hz, J3=15.6 Hz, 1H), 7.52 (t, J=7.4 Hz, 2H), 7.42 (t, J=7.5 Hz, 1H), 7.34 (d, J=7.4 Hz, 3H), 7.28-7.25 (m, 2H), 7.22-7.18 (m, 2H), 7.10-7.02 (m, 4H), 6.79 (d, J=7.9 Hz, 1H). 13C NMR (100 MHz, CDCl3) δ 173.55, 159.02, 155.16, 149.44, 144.79, 137.17, 134.25, 130.25, 129.71, 129.23, 128.75, 128.57, 128.37, 126.72, 125.91, 124.07, 123.51, 123.24, 121.44, 121.12, 110.10, 86.44. HRMS calculated [M+H]+ for C25H19O2N2: 379.1441. found: 379.1445. FTIR (cm-1) 3368, 2918, 2824, 1682, 1602, 1492, 1454, 1407, 1353, 1284, 1253, 1169, 1112, 1026, 955, 765.

Example 28

5-methoxy-1-methyl-3-phenoxy-3-(pyridin-2-yl)indolin-2-one (8e)

Following the general procedure, treatment of pyridine 7a (0.060 g, 60 μL, 0.75 mmol) and 5-methoxy-1-methylindoline-2,3-dione (0.096 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane 0.396 g, 1.50 mmol) in THF (2.0 mL) at 30° C. for 12 h followed by flash column chromatography (Pet. ether/EtOAc=60/40) of the crude reaction mixture afforded 5-methoxy-1-methyl-3-phenoxy-3-(pyridin-2-yl)indolin-2-one 8e as a yellow solid (0.133 g, 77%).

Rf (Pet. ether/EtOAc=50/50): 0.48; 1H NMR (400 MHz, CDCl3) δ 8.47-8.46 (m, 1H), 8.13-8.11 (m, 1H), 7.81 (dt, J1=1.7 Hz, J2=7.7 Hz, J3=15.7 Hz, 1H), 7.23-7.20 (m, 1H), 7.12 (t, J=7.3 Hz, 2H), 6.96 (t, J=7.3 Hz, 1H), 6.87-6.81 (m, 4H), 6.75 (d, J=8.4 Hz, 1H), 3.71 (s, 3H, CH3), 3.21 (s, 3H, CH3). 13C NMR (100 MHz, CDCl3) δ 173.16, 158.98, 156.30, 155.28, 149.42, 137.93, 137.21, 130.04, 129.28, 126.68, 123.67, 123.23, 121.10, 120.61, 114.73, 112.72, 109.36, 106.01, 86.41, 55.86, 26.77. HRMS calculated [M+H]+ for C21H19O3N2: 347.1390. found: 347.1393. FTIR (cm-1) 3006, 2873, 1698, 1638, 1599, 1492, 1449, 1350, 1289, 1253, 1163, 1034, 900, 952, 845, 755, 702, 661.

Example 29

5-Bromo-1-methyl-3-phenoxy-3-(pyridin-2-yl)indolin-2-one (8f)

Following the general procedure, treatment of pyridine 7a (0.060 g, 60 μL, 0.75 mmol) and 5-bromo-1-methylindoline-2,3-dione (0.120 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=70/30) of the crude reaction mixture afforded 5-bromo-1-methyl-3-phenoxy-3-(pyridin-2-yl)indolin-2-one 8f as a yellow solid (0.146 g, 74%).

Rf (Pet. ether/EtOAc=50/50): 0.65; 1H NMR (400 MHz, CDCl3) δ 8.44 (d, J=4.4 Hz, 1H), 8.13 (d, J=8.0 Hz, 1H), 7.83 (dt, J=1.3 Hz, J2=7.8 Hz, J3=15.5 Hz, 1H), 7.41 (dd, J1=1.7 Hz, J2=8.3 Hz, 1H), 7.31 (m, 1H), 7.24-7.21 (m, 1H), 7.15 (t, J=7.7 Hz, 2H), 6.99 (t, J=7.3 Hz, 1H), 6.86 (d, J=8.1 Hz, 2H), 6.71 (d, J=8.3 Hz, 1H), 3.20 (s, 3H, CH3). 13C NMR (100 MHz, CDCl3) δ 173.68, 158.36, 154.90, 149.39, 143.51, 137.38, 133.15, 130.79, 129.39, 128.53, 124.00, 123.47, 121.01, 120.65, 115.74, 110.43, 85.90, 26.74. HRMS calculated [M+H]+ for C20H16O2N2Br: 395.0390. found: 395.0393. FTIR (cm-1) 3061, 2926, 1732, 1607, 1588, 1489, 1466, 1434, 1358, 1340, 1237, 1213, 1100, 1053, 1032, 994, 971, 752, 694.

Example 30

5-Chloro-1-methyl-3-phenoxy-3-(pyridin-2-yl)indolin-2-one (8g)

Following the general procedure, treatment of pyridine 7a (0.060 g, 60 μL, 0.75 mmol) and 5-chloro-1-methylindoline-2,3-dione (0.098 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. Ether/EtOAc=70/30) of the 1730, 1611, 1588, 1489, 1467, 1434, 1359, 1210, 1173, 1077, 1050, 1028, 993, 965, 783, 751, 695, 550.

crude reaction mixture afforded 5-chloro-1-methyl-3-phenoxy-3-(pyridin-2-yl)indolin-2-one 8g as a yellow solid (0.120 g, 68% yield).

Rf (Pet. ether/EtOAc=50/50): 0.65; 1H NMR (400 MHz, CDCl3) δ 8.47-8.46 (m, 1H), 8.15 (d, J=8.0 Hz, 1H), 7.85 (dt, J1=1.8 Hz, J2=7.8 Hz, J3=15.5 Hz, 1H), 7.30-7.23 (m, 2H), 7.20-7.14 (m, 3H), 7.00 (t, J=7.5 Hz, 1H), 6.89 (d, J=7.9 Hz, 2H), 6.77 (d, J=8.3 Hz, 1H), 3.23 (s, 3H, CH3). 13C NMR (100 MHz, CDCl3) δ 173.81, 158.40, 154.96, 149.39, 143.07, 137.36, 130.46, 130.27, 129.38, 128.48, 125.87, 124.00, 123.45, 121.05, 120.70, 109.91, 85.99, 26.75. HRMS calculated [M+H]+ for C20H16O2N2Cl: 351.0895. found: 351.0894. FTIR (cm-1) 2926, 2855, 1723, 1635, 1584, 1539, 1410, 1377, 1351, 1302, 1279, 1257, 1229, 1159, 1085, 997, 769, 746, 712, 657.

Example 31

5-Fluoro-1-methyl-3-phenoxy-3-(pyridin-2-yl)indolin-2-one (8h)

Following the general procedure, treatment of pyridine 7a (0.060 g, 60 μL, 0.75 mmol) and 5-fluoro-1-methylindoline-2,3-dione (0.090 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=75/25) of the crude reaction mixture afforded 5-fluoro-1-methyl-3-phenoxy-3-(pyridin-2-yl)indolin-2-one 8 h as a yellow solid (0.114 g, 68%).

Rf (Pet. ether/EtOAc=50/50): 0.68; 1H NMR (400 MHz, CDCl3) δ 8.48 (d, J=4.7 Hz, 1H), 8.17 (d, J=8.0 Hz, 1H), 7.86 (dt, J1=1.6 Hz, J2=7.8 Hz, J3=15.6 Hz, 1H), 7.29-7.25 (m, 1H), 7.17 (t, J=7.7 Hz, 2H), 7.06-6.98 (m, 3H), 6.91-6.89 (m, 2H), 6.79 (dd, J1=4.0 Hz, J2=8.5 Hz, 1H), 3.25 (s, 3H, CH3). 13C NMR (100 MHz, CDCl3) δ 174.03, 159.52 (d, J=219.2 Hz), 158.20, 155.02, 149.40, 140.49, 137.36, 130.32 (d, J=7.6 Hz), 129.37, 123.73 (d, J=55.0 Hz), 121.16, 120.78, 116.70 (d, J=23.4 Hz), 113.64 (d, J=25.5 Hz), 109.54 (d, J=7.8 Hz), 86.20, 26.81. HRMS calculated [M+H]+ for C20H16O2N2F: 335.1190. found: 335.1183. FTIR (cm-1) 3060, 2937, 1732, 1618, 1588, 1492, 1469, 1435, 1347, 1270, 1237, 1213, 1152, 1129, 1106, 1051, 1032, 995, 971, 870, 813, 762, 694, 621.

Example 32

3-(4-(Dimethylamino)pyridin-2-yl)-1-methyl-3-phenoxyindolin-2-one (8i)

Following the general procedure, treatment of N,N-dimethylpyridin-4-amine 7i (0.092 g, 0.75 mmol) and 1-methylindoline-2,3-dione (0.080 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. ether/EtOAc=30/70) of the crude reaction mixture afforded 3-(4-(dimethylamino)pyridin-2-yl)-1-methyl-3-phenoxyindolin-2-one 8i as a white solid (0.160 g, 89%).

Rf (Pet. ether/EtOAc=50/50): 0.32; 1H NMR (400 MHz, CDCl3) δ 8.08 (d, J=5.9 Hz, 1H), 7.40 (d, J=2.5 Hz, 1H), 7.30-7.25 (m, 1H), 7.23 (d, J=7.4 Hz, 1H), 7.11 (t, J=7.6 Hz, 2H), 7.02-6.93 (m, 2H), 6.89-6.87 (m, 2H), 6.80 (d, J=7.8 Hz, 1H), 6.39 (dd, J1=2.5 Hz, J2=5.9 Hz, 1H), 3.22 (s, 3H, CH3), 3.22 (s, 6H, 2CH3). 13C NMR (100 MHz, CDCl3) δ 174.60, 158.84, 155.33, 155.25, 149.59, 144.63, 130.14, 129.11, 125.38, 123.73, 122.97, 121.30, 108.85, 105.96, 103.57, 86.41, 39.39, 26.64. HRMS calculated [M+H]+ for C22H22O2N3: 360.1707. found: 360.1704. FTIR (cm-1) 3054, 2865, 1959, 1729, 1599, 1542, 1489, 1469, 1451, 1352, 1296, 1251, 1123, 1036, 984, 948, 859, 756, 696.

Example 33

3-(3,4-Difluorophenoxy)-1-methyl-3-(pyridin-2-yl)indolin-2-one (8j)

Following the general procedure, treatment of pyridine 7a (0.030 g, 30 μL, 0.375 mmol) and 1-methylindoline-2,3-dione (0.040 g, 0.25 mmol) with 4,5-difluoro-2-(trimethylsilyl)phenyl trifluoromethanesulfonate 2d (0.125 g, 0.375 mmol) in the presence of KF (0.043 g, 0.75 mmol) and (0.198 g, 1,4,7,10,13,16-hexaoxacyclooctadecane 0.75 mmol) in THF (1.0 mL) at 30° C. for 12 h followed by flash column chromatography (Pet. ether/EtOAc=80/20) of the crude reaction mixture afforded 3-(3,4-difluorophenoxy)-1-methyl-3-(pyridin-2-yl)indolin-2-one 8j as a yellow solid (0.63 g, 71%).

Rf (Pet. ether/EtOAc=50/50): 0.71; 1H NMR (400 MHz, CDCl3) δ 8.46 (d, J=4.2 Hz, 1H), 8.04 (d, J=8.0 Hz, 1H), 7.81 (dt, J1=1.8 Hz, J2=7.7 Hz, J3=15.5 Hz, 1H), 7.35-7.32 (m, 1H), 7.22 (t, J=5.6 Hz, 2H), 7.05 (t, J=7.5 Hz, 1H), 6.93-6.84 (m, 2H), 6.76-6.70 (m, 1H), 6.64-6.61 (m, 1H), 3.23 (s, 3H, CH3). 13C NMR (100 MHz, CDCl3) δ 173.65, 158.27, 151.10 (m), 149.49, 147.28 (dd, J1=7.8 Hz, J2=252.1 Hz), 147.18 (dd, J1=7.5 Hz, J2=256.0 Hz), 144.49, 137.27, 130.81, 127.99, 125.58, 123.40, 121.01, 127.29 (m), 116.94 (d, J=19.0 Hz), 111.15 (d, J=19.2 Hz), 109.18, 86.90, 26.70. HRMS calculated [M+H]+ for C20H15O2N2F2: 353.1096. found: 353.1096. FTIR (cm-1) 2926, 1742, 1685, 1611, 1512, 1492, 1472, 1430, 1369, 1328, 1252, 1214, 1159, 1117, 1093, 865, 754.

Example 34

1-(Benzo[d][1,3]dioxol-5-yl)pyridin-2(1H)-one (9a)

Following the general procedure, treatment of pyridine 7a (0.020 g, 20 μL, 0.25 mmol) with 6-(trimethylsilyl)benzo[d][1,3]dioxol-5-yl trifluoromethanesulfonate 2c (0.086 g, 0.25 mmol) in the presence of KF (0.029 g, 0.50 mmol) and 1,4,7,10,13,16-hexaoxacyclooctadecane (0.132 g, 0.50 mmol) in THF (1.0 mL) at 30° C. for 12 h followed by flash column chromatography (Pet. ether/EtOAc=30/70) of the crude reaction mixture afforded 1-(benzo[d][1,3]dioxol-5-yl)pyridin-2(1H)-one 9a as a brown solid (0.043 g, 79%). CCDC-938923 (9a), contains the supplementary crystallographic data for this paper.

Rf (Pet. ether/EtOAc=30/70): 0.30; 1H NMR (400 MHz, CDCl3) δ 7.39-7.34 (m, 1H), 7.29-7.28 (m, 1H), 6.87-6.85 (m, 2H), 6.76 (dd, J1=1.8 Hz, J2=8.2 Hz, 1H), 6.62 (d, J=9.3 Hz, 1H), 6.20 (t, J=6.7 Hz, 1H), 6.01 (s, 2H, CH2). 13C NMR (100 MHz, CDCl3) δ 162.71, 148.15, 147.82, 139.96, 138.36, 134.90, 121.84, 119.91, 108.48, 105.91, 101.98. HRMS calculated [M+H]+ for C12H10O3N: 216.0655. found: 216.0652. FTIR (cm-1) 2901, 1716, 1667, 1611, 1593, 1533, 1504, 1456, 1444, 1355, 1250, 1193, 1141, 1104, 1037, 1004, 933, 902, 841, 810, 761, 735, 639.

Example 35

1-(3,4-Dimethylphenyl)pyridin-2(1H)-one (9b)

Following the general procedure, treatment of pyridine 7a (0.020 g, 20 μL, 0.25 mmol) with 4,5-dimethyl-2-(trimethylsilyl)phenyl trifluoromethane sulfonate 2b (0.082 g, 0.25 mmol) in the presence of KF (0.029 g, 0.50 mmol) and 1,4,7,10,13,16-hexaoxacyclooctadecane (0.132 g, 0.50 mmol) in THF (1.0 mL) at 30° C. for 12 h followed by flash column chromatography (Pet. ether/EtOAc=40/60) of the crude reaction mixture afforded 1-(3,4-dimethylphenyl)pyridin-2(1H)-one 9b as a yellow solid (0.035 g, 70%).

Rf (Pet. ether/EtOAc=30/70): 0.38; 1H NMR (400 MHz, CDCl3) δ 7.40-7.35 (m, 1H), 7.30 (dd, J1=1.8 Hz, J2=6.8 Hz, 1H), 7.23 (d, J=7.9 Hz, 1H), 7.14 (d, J=1.8 Hz, 1H), 7.08 (dd, J1=2.0 Hz, J2=7.9 Hz, 1H), 6.63 (d, J=9.3 Hz, 1H), 6.21 (t, J=6.7 Hz, 1H), 2.29 (s, 6H, 2CH3). 13C NMR (100 MHz, CDCl3) δ 162.75, 139.85, 138.75, 138.33, 137.94, 137.32, 130.51, 127.55, 123.74, 121.85, 105.78, 19.96, 19.59. HRMS calculated [M+H]+ for C13H14ON: 200.1070. found: 200.1067. FTIR (cm-1) 2922, 1668, 1594, 1534, 1504, 1471, 1453, 1384, 1373, 1347, 1295, 1277, 1141, 1121, 1021, 990, 838, 761, 730, 611.

Example 36

1-Methyl-3-(phenoxy-2-d)-3-(pyridin-2-yl-d4)indolin-2-one (12)

Following the general procedure, treatment of pyridine-d5 11 (0.063 g, 60 μL, 0.75 mmol) and 1-methylindoline-2,3-dione (0.080 g, 0.50 mmol) with 2-(trimethylsilyl)phenyl trifluoromethane sulfonate 2a (0.223 g, 182 μL, 0.75 mmol) in the presence of KF (0.087 g, 1.50 mmol) and 1,4,7,10,13,16-hexaoxacyclooctadecane (0.396 g, 1.50 mmol) in THF (2.0 mL) at 30° C. for 12 h followed by flash column chromatography (Pet. Ether/EtOAc=65/35) of the crude reaction mixture afforded 1-methyl-3-(phenoxy-2-d)-3-(pyridin-2-yl-d4)indolin-2-one 12 as a yellow solid (0.105 g, 65% yield).

Rf (Pet. ether/EtOAc=50/50): 0.61; 1H NMR (400 MHz, CDCl3) 7.30 (dt, J1=1.4 Hz, J2=7.8 Hz, J3=15.6 Hz, 1H), 7.20 (d, J=7.4 Hz, 1H), 7.13-7.10 (m, 2H), 7.01 (d, J=7.7 Hz, 1H), 6.95 (t, J=7.4 Hz, 1H), 6.88-6.86 (m, 1H), 6.83 (d, J=7.8 Hz, 1H), 3.23 (s, 3H, CH3). 13C NMR (100 MHz, CDCl3) δ 174.27, 158.97, 155.21, 155.16, 144.51, 130.34, 129.21, 129.10, 128.72, 125.53, 123.71, 123.11, 120.81, 108.91, 86.24, 26.65. HRMS calculated [M+H]+ for C20H102H5O2N2Na: 343.1340. found: 343.1348. FTIR (cm-1) 2925, 2854, 1728, 1611, 1491, 1470, 1422, 1372, 1348, 1329, 1302, 1231, 1211, 1168, 1091, 1028, 972, 752.

ADVANTAGES OF THE INVENTION

Novel biologically active spiro-oxazines and Indolinones compounds

High yield and selectivity of the products by the instant process

Industrially and economically feasible process

We claim:
1. Novel spiro-oxazino compounds of Formula-I

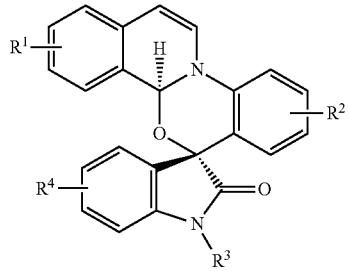

Formula I wherein $R^1$ is selected from the group consisting of H, Cl, Br, F and I; $R^2$ is selected from ($C_1$-$C_6$) alkyl, fluoro, or dioxane ring O—($CH_2$)—O; $R^3$ represents ($C_1$-$C_6$) alkyl, aryl, arylalkyl, or allyl; and $R^4$ is halogen, ($C_1$-$C_6$) alkoxy, $NO_2$, ($C_2$-$C_6$) alkylene, ($C_1$-$C_6$) alkylaryl, or aralkyl;

the spiro-oxazino compound selected from the group consisting of:

i. 5'-bromo-1'-methyl-4bH-spiro[benzo[4,5][1,3]oxazino[2,3-a]isoquinoline-6,3'-indolin]-2'-one (4a);
ii. 1'-Methyl-4bH-spiro[benzo[4,5][1,3]oxazino[2,3-a]isoquinoline-6,3'-indolin]-2'-one (4b);
iii. 1'-Benzyl-4bH-spiro[benzo[4,5][1,3]oxazino[2,3-a]isoquinoline-6,3'-indolin]-2'-one (4c);
iv. 1'-Allyl-4bH-spiro[benzo[4,5][1,3]oxazino[2,3-a]isoquinoline-6,3'-indolin]-2'-one (4d);
v. 1'-Phenyl-4bH-spiro[benzo[4,5][1,3]oxazino[2,3-a]isoquinoline-6,3'-indolin]-2'-one (4e);
vi. 5'-Methoxy-1'-methyl-4bH-spiro[benzo[4,5][1,3]oxazino[2,3-a]isoquinoline-6,3' indolin]-2'-one (4f);
vii. 5'-Chloro-1'-methyl-4bH-spiro[benzo[4,5][1,3]oxazino[2,3-a]isoquinoline-6,3'-indolin]-2'-one (4g);
viii. 5'-fluoro-1'-methyl-4bH-spiro[benzo[4,5][1,3]oxazino[2,3-a]isoquinoline-6,3'-indolin]-2'-one (4h);
ix. 1',8,9-Trimethyl-4bH-spiro[benzo[4,5][1,3]oxazino[2,3-a]isoquinoline-6,3'-indolin]-2'-one (4i);
x. I-Methyl-4b'H-spiro[indoline-3,6'-[,3]dioxolo[4",5":4',5']benzo[1',2':4,5][1,3]oxazino[2,3-a]isoquinolin]-2-one (4j);
xi. 8,9-Difluoro-1'-methyl-4bH-spiro[benzo[4,5][1,3]oxazino[2,3-a]isoquinoline-6,3' indolin]-2'-one (4k);
xii. 1-Methyl-13b'H-spiro[indoline-3,15'-naphtho[2',1':4,5][1,3]oxazino[2,3-a]isoquinolin]-2-one (4l);
xiii. 1-Bromo-1'-methyl-4bH-spiro[benzo[4,5][1,3]oxazino[2,3-a]isoquinoline-6,3'-indolin]-2'-one (4m);
xiv. 1'-Methyl-6aH-spiro[benzo[4,5][1,3]oxazino[3,2-a]quinoline-5,3'-indolin]-2'-one (4n); and
xv. 1'-Benzyl-6aH-spiro[benzo[4,5][1,3]oxazino[3,2-a]quinoline-5,3'-indolin]-2'-one (4o).

2. A transitional-metal free, multicomponent reaction (MCR) process for the preparation of novel spiro-oxazino compounds of Formula I comprising nucleophile triggered coupling of aryne precursor and N-substituted isatin, at temperature range of 20° to 100° C., in presence of fluoride source selected from KF and phase transfer catalyst selected from in an organic solvent to afford spiro-oxazine compounds of formula I.

3. A process according to claim 2, wherein the nucleophile is heterocyclic or heteroaromatic compound selected from the group consisting of substituted or unsubstituted pyridine, quinolone, isoquinoline and wherein, the substituents are selected from halogen, or secondary amine.

4. A process according to claim 2, wherein the N-substituted isatin having formula (3)

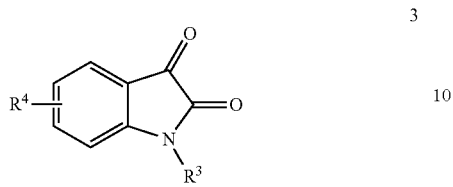

where $R^3$ represents $(C_1-C_6)$ alkyl, aryl, arylalkyl, or allyl; and $R^4$ is halogen, $(C_1-C_6)$ alkoxy, $NO_2$, $(C_2-C_6)$ alkylene, $(C_1-C_6)$ alkyl, aryl, or aralkyl.

5. A process according to claim 2, wherein the aryne precursor is substituted or unsubstituted 2-(trimethylsilyl) aryl triflate.

6. A process according to claim 2, wherein the organic solvent is selected from the group THF, Ethyl acetate, DMF, DCM, Acetone and mixtures thereof.

7. A-process according to claim 2, wherein the temperature maintained during the course of reaction is 25° to 75° C.

* * * * *